US009617539B2

(12) United States Patent
Rigo et al.

(10) Patent No.: US 9,617,539 B2
(45) Date of Patent: Apr. 11, 2017

(54) MODULATION OF UBE3A-ATS EXPRESSION

(71) Applicants: Ionis Pharmaceuticals, Inc., Carlsbad, CA (US); Baylor College of Medicine, Houston, TX (US)

(72) Inventors: Frank Rigo, Carlsbad, CA (US); Amanda Ward, Carlsbad, CA (US); Linyan Meng, Houston, TX (US); Arthur L. Beaudet, Houston, TX (US)

(73) Assignees: Ionis Pharmaceuticals, Inc., Carlsbad, CA (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 14/409,348

(22) PCT Filed: Jun. 25, 2013

(86) PCT No.: PCT/US2013/047701
§ 371 (c)(1),
(2) Date: Dec. 18, 2014

(87) PCT Pub. No.: WO2014/004572
PCT Pub. Date: Jan. 3, 2014

(65) Prior Publication Data
US 2015/0191723 A1 Jul. 9, 2015

Related U.S. Application Data

(60) Provisional application No. 61/772,925, filed on Mar. 5, 2013, provisional application No. 61/755,617, filed on Jan. 23, 2013, provisional application No. 61/750,939, filed on Jan. 10, 2013, provisional application No. 61/738,959, filed on Dec. 18, 2012, provisional application No. 61/664,083, filed on Jun. 25, 2012.

(51) Int. Cl.
*C12N 15/11* (2006.01)
*C12N 15/113* (2010.01)
*C07H 21/04* (2006.01)

(52) U.S. Cl.
CPC ........ *C12N 15/113* (2013.01); *C12N 2310/11* (2013.01); *C12N 2310/111* (2013.01); *C12N 2310/113* (2013.01); *C12N 2310/315* (2013.01); *C12N 2310/321* (2013.01); *C12N 2310/323* (2013.01); *C12N 2310/3341* (2013.01); *C12N 2310/341* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 4,981,957 A | 1/1991 | Lebleu et al. | |
| 5,034,506 A | 7/1991 | Summerton et al. | |
| 5,118,800 A | 6/1992 | Smith et al. | |
| 5,166,315 A | 11/1992 | Summerton et al. | |
| 5,185,444 A | 2/1993 | Summerton et al. | |
| 5,319,080 A | 6/1994 | Leumann | |
| 5,359,044 A | 10/1994 | Cook et al. | |
| 5,393,878 A | 2/1995 | Leumann | |
| 5,446,137 A | 8/1995 | Maag et al. | |
| 5,466,786 A | 11/1995 | Buhr et al. | |
| 5,514,785 A | 5/1996 | Van Ness et al. | |
| 5,519,134 A | 5/1996 | Acevedo et al. | |
| 5,567,811 A | 10/1996 | Misiura et al. | |
| 5,576,427 A | 11/1996 | Cook et al. | |
| 5,591,722 A | 1/1997 | Montgomery et al. | |
| 5,597,909 A | 1/1997 | Urdea et al. | |
| 5,610,300 A | 3/1997 | Altmann et al. | |
| 5,627,053 A | 5/1997 | Usman et al. | |
| 5,639,873 A | 6/1997 | Barascut et al. | |
| 5,646,265 A | 7/1997 | McGee | |
| 5,670,633 A | 9/1997 | Cook et al. | |
| 5,698,685 A | 12/1997 | Summerton et al. | |
| 5,700,920 A | 12/1997 | Altmann et al. | |
| 5,792,847 A | 8/1998 | Buhr et al. | |
| 5,801,154 A | 9/1998 | Baracchini et al. | |
| 6,184,212 B1 * | 2/2001 | Miraglia | C07H 21/00 435/325 |
| 6,268,490 B1 | 7/2001 | Imanishi et al. | |
| 6,300,132 B1 * | 10/2001 | Monia | C12N 15/113 435/375 |

(Continued)

FOREIGN PATENT DOCUMENTS

| | | | |
|---|---|---|---|
| DE | EP 1764108 A1 * | 3/2007 | ............. A61K 39/39 |
| WO | WO 98/39352 | 9/1998 | |

(Continued)

OTHER PUBLICATIONS

*Homo sapiens* ubiquitin protein ligase E3A (human papilloma virus E6-associated protein, Angelman syndrome) (UBE3A), mRNA, GenBank NM_000462.1, Jan. 11, 2011, accessed and retrieved from www.ncbi.nlm.nih.gov on May 23, 2016.*
Church et al., "Lineage-specific biology revealed by a finished genome assembly of the mouse" PLoS Biol. (2009) 7: e1000112.
King et al., "Topoisomerases facilitate transcription of long genes linked to autism" Nature (2013) 501: 58-62.
Plagge "Non-Coding RNAs at the Gnas and Snrpn-Ube3a Imprinted Gene Loci and Their Involvement in Hereditary Disorders" Front Genet. (2012) 3: 1-6.
Powell et al., "R-loop formation at Snord116 mediates topotecan inhibition of Ube3a-antisense and allele-specific chromatin decondensation" Proc Natl Acad Sci (2013) 110: 13938-43.

(Continued)

*Primary Examiner* — Dana Shin
(74) *Attorney, Agent, or Firm* — Ionis Pharmaceuticals, Inc. Patent Dept.

(57) ABSTRACT

Certain embodiments are directed to methods and compounds for inhibiting UBE3A-ATS, the endogenous antisense transcript of ubiquitin protein ligase E3A (UBE3A). Such methods and compounds are useful for inducing expression of paternal UBE3A in cells and animals.

16 Claims, 2 Drawing Sheets

(56) References Cited

U.S. PATENT DOCUMENTS

| | | | |
|---|---|---|---|
| 6,525,191 B1 | 2/2003 | Ramasamy | |
| 6,582,908 B2 | 6/2003 | Fodor et al. | |
| 6,600,032 B1 | 7/2003 | Manoharan et al. | |
| 6,617,162 B2* | 9/2003 | Dobie | C12N 15/1138 435/325 |
| 6,670,461 B1 | 12/2003 | Nielsen et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,696,345 B2 | 4/2010 | Allerson et al. | |
| 2001/0053519 A1 | 12/2001 | Fodor et al. | |
| 2003/0087855 A1* | 5/2003 | Ward | C12N 15/1137 514/44 A |
| 2003/0228597 A1 | 12/2003 | Cowsert et al. | |
| 2004/0171570 A1 | 9/2004 | Allerson et al. | |
| 2005/0130923 A1 | 6/2005 | Bhat et al. | |
| 2007/0031844 A1 | 2/2007 | Khvorova et al. | |
| 2008/0039618 A1 | 2/2008 | Allerson et al. | |
| 2008/0108583 A1* | 5/2008 | Feinstein | A61K 31/7088 514/44 A |
| 2009/0012281 A1 | 1/2009 | Swayze et al. | |
| 2013/0225659 A1 | 8/2013 | Bennett et al. | |
| 2014/0315992 A1 | 10/2014 | Hakonarson et al. | |

FOREIGN PATENT DOCUMENTS

| | | |
|---|---|---|
| WO | WO 99/14226 | 3/1999 |
| WO | WO 00/63364 | 10/2000 |
| WO | WO 01/49687 | 7/2001 |
| WO | WO 01/92582 | 12/2001 |
| WO | WO 2003/004602 | 1/2003 |
| WO | WO 2004/035765 | 10/2003 |
| WO | WO 2004016754 A2 * | 2/2004 ......... C12N 15/1138 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2011/109398 | 9/2011 |
| WO | WO 2011/139702 | 11/2011 |
| WO | WO 2012/012467 | 1/2012 |
| WO | WO 2012/064806 | 5/2012 |
| WO | WO 2013/033230 | 3/2013 |

OTHER PUBLICATIONS

Runte et al., "The IC-SNURF-SNRPN Transcript serves as a Host for Multiple Small Nucleolar RNA Species and as an Antisense RNA for UBE3A" Human Molecular Genetics (2001) 10: 2687-2700.
International Search Report for application PCT/US2013/47701 dated Feb. 14, 2014, 21 pages.
International Search Report for application PCT/US2015/062622 dated Jan. 15, 2016, 14 pages.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Allshire, "Molecular biology. RNAi and heterochromatin—a hushed-up affair" Science (2002) 297(5588):1818-1819.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals " Chimia. (1996) 50(4):168-176.
Altmann et al., "Second-generation antisense oligonucleotides: structure—activity relationships and the design of improved signal-transduction inhibitors" Biochem. Soc. Trans. (1996) 24:630-637.
Altschul et al., "Basic Local Alignment Search Tool" J. Mol. Biol. (1990) 215:403-410.
Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Braasch et al., "Locked nucleic acid (LNA): fine-tuning the recognition of DNA and RNA" Chem. Biol. (2001) 8:1-7.
Braasch et al., "Novel antisense and peptide nucleic acid strategies for controlling gene expression" Biochemistry (2002) 41(14):4503-4510.
Branch et al., "A good antisense molecule is hard to find," TIBS (1998) 23:45-50.
Cattanach et al., "A candidate model for Angelman syndrome in the mouse" Mamm. Genome (1997) 8(7):472-478.
Chen et al., "Motor coordination deficits in Alpk1 mutant mice with the inserted piggyBac transposon" BMC Neruosci. (2011) 12:1.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clark et al., "Purkinje cell expression of a mutant allele of SCA1 in transgenic mice leads to disparate effects on motor behaviors, followed by a progressive cerebellar dysfunction and histological alterations" J. Neurosci. (1997) 17(19):7385-7395.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Dindot et al., "The Angelman syndrome ubiquitin ligase localizes to the synapse and nucleus, and maternal deficiency results in abnormal dendritic spine morphology" Hum. Mol. Genet. (2008) 17(1):111-118.
Elayadi et al., "Application of PNA and LNA oligomers to chemotherapy" Curr. Opinion Invens. Drugs (2001) 2:558-561.
Faghihi et al., "RNAi screen indicates widespread biological function for human natural antisense transcripts" PLoS One (2010) 5(10):e13177.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al., "Activity of a novel bc1-2/bc1-xLbispecific antisense oligonucleotide against tumors of diverse histologic origins" J. Natl. Cancer Inst. (2001) 93:463-471.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Hall et al., "Establishment and maintenance of a heterochromatin domain" Science (2002) 297(5590):2232-2237.
Hawkins et al., "Transcriptional regulation of Oct4 by a long non-coding Rna antisense to Oct4-pseudogene 5" Transcription (2010) 1(3):165-175.

(56) References Cited

OTHER PUBLICATIONS

Horvath et al., "Stereoselective synthesis of (-)-ara-cyclohexenyl-adenine" Tetrahedron Letters (2007) 48:3621-3623.

Huang et al., "Topoisomerase inhibitors unsilence the dormant allele of Ube3a in neurons" Nature (2011) 481(3780): 185-189.

Jenuwein, "Molecular biology. An RNA-guided pathway for the epigenome" Science (2002) 297(5590):2215-2218.

Hang et al., "Mutation of the Angelman ubiquitin ligase in mice causes increased cytoplasmic p53 and deficits of contextual learning and long-term potentiation" Neruon (1998) 21(4):799-811.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Manoharan et al., "Chemical Modifications to Improve Uptake and Bioavailability of Antisense Oligonucleotides" Ann. N.Y. Acad. Sci. (1992) 660: 306-309.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Martin, "New acces to 2'-O-alkylated ribonucleosides and properties of 2'-O-alkylated oligoribonucleotides" Helv. Chim. Acta. (1995) 78:486-504.

Meng et al., "Ube3a-ATS is an atypical RNA polymerase II transcript that represses the paternal expression of Ube3a" Hum. Mol. Genet. (2012) 21(13):3001-3012.

Miller et al., "Phenotypic characterization of a genetically diverse panel of mice for behavioral despair and anxiety" PLoS One (2010) 5(12):e14458.

Mishra et al., "Improved leishmanicidal effect of phosphorotioate antisense oligonucleotides by LDL-mediated delivery" Biochim. Biophys. Acta (1995) 1264:229-237.

Modarresi et al., "Inhibition of natural antisense transcripts in vivo results in gene-specific transcriptional upregulation" Nat. Biotechnol. (2012) 30(5):453-459.

Morris et al., "Bidirectional transcription directs both transcriptional gene activation and suppression in human cells" PLoS Genet. (2008) 4(11):e1000258.

Nauwelaerts et al., "Cyclohexenyl nucleic acids: conformationally flexible oligonucleotides" Nucleic Acids Res. (2005) 33(8):2452-2463.

Nauwelaerts et al., "Structural characterization and biological evaluation of small interfering RNAs containing cyclohexenyl nucleosides" J. Am. Chem. Soc. (2007) 129(30):9340-9348.

New England Biolabs 1998/99 Catalog (cover page and pp. 121 and 284).

Njung'e et al., "Evaluation of marble-burying behavior as a model of anxiety" Pharmacol. Biochem. Behav. (1991) 38(1):63-67.

Oberhauser et al., "Effective incorporation of 2'-0-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Pal-Bhadra et al., "Heterochromatic silencing and HP1 localization in Drosophila are dependent on the RNAi machinery" Science (2004) 303(5658):669-672.

Reynolds et al., "Rational siRNA design for RNA interference" Nature Biotechnology (2004) 22(3):326-330.

Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.

Robeyns et al., "Structure of the fully modified left-handed cyclohexene nucleic acid sequence GTGTACAC" J. Am. Chem. Soc. (2008) 130(6):1979-1984.

Sahoo et al., "Prader-Willi phenotype caused by paternal deficiency for the HBII-85 C/D box small nucleolar RNA cluster" Nat. Genet. (2008) 40(6):719-721.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Smith et al., "Comparison of biosequences" Adv. Appl. Math. (1981) 2(4):482-489.

Srivastava et al., "Five- and Six-Membered Conformationally Locked 2',4'-Carbocyclic riboThymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tsai et al., "Paternal deletion from Snrpn to Ube3a in the mouse causes hypotonia, growth retardation and partial lethality and provides evidence for a gene contributing to Prader-Willi syndrome" Hum. Mol. Genet. (1999) 8(8):1357-1364.

Verbeure et al., "RNase H mediated cleavage of RNA by cyclohexene nucleic acid (CeNA)" Nucleic Acids Res. (2001) 29(24):4941-4947.

Verdel et al., "RNAi-mediated targeting of heterochromatin by the RITS complex" Science (2004) 303(5668):672-676.

Volpe et al., "Regulation of heterochromatic silencing and histone H3 lysine-9 methylation by RNAi" Science (2002) 297(5588):1833:1837.

Wahlestedt et al., "Potent and nontoxic antisense oligonucleotide containing locked nucleic acids" Proc. Natl. Acad. Sci. USA (2000) 97: 5633-5638.

Wang et al., "A straightforward stereoselective synthesis of D- and L-5-hydroxy-4-hydroxymethyl-2- cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

(56) References Cited

OTHER PUBLICATIONS

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Williams et al., "Clinical and genetic aspects of Angelman syndrome" Genet. Med. (2010) 12(7):385-395.

Woolf et al., "Specificity of antisense oligonucleotides in vivo" Proc. Natl. Acad. Sci. (1992) 89(16):7305-7309.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Meng et al., "Towards a therapy for Angelman syndrome by targeting a long non-coding RNA" Nature (2015) 518:409-412.

Beaudet et al., "Angelman syndrome: Drugs to awaken a paternal gene," Nature (2011) 481: 150-152.

Meng et al.,"Truncation of Ube3a-ATS Unsilences Paternal UBE3a and Ameliorates Behavioral Defects in the Angelman Syndrome Mouse Model" PLOS Genetics (2013) 9:e1004039.

International Search report for application EP 2864479 dated May 10, 2016.

\* cited by examiner

MODULATION OF UBE3A-ATS EXPRESSION

CROSS REFERENCED TO RELATED APPLICATIONS

This application is a U.S. National Phase filing under 35 U.S.C. §371 claiming priority to International Serial No. PCT/US2013/047701 filed Jun. 25, 2013, which claims priority to U.S. Provisional Application 61/772,925, filed Mar. 5, 2013, U.S. Provisional Application 61/755,617, filed Jan. 23, 2013, U.S. Provisional Application 61/750,939, filed Jan. 10, 2013, U.S. Provisional Application 61/738,959, filed Dec. 18, 2012, and U.S. Provisional Application 61/664,083, filed Jun. 25, 2012, each of which is incorporated herein by reference in its entirety.

STATEMENT OF GOVERNMENT SUPPORT

This invention was made with government support under R01HD037283 awarded by National Institute of Health. The government has certain rights in the invention.

SEQUENCE LISTING

The present application is being filed along with a Sequence Listing in electronic format. The Sequence Listing is provided as a file entitled BIOL0204USASEQ_ST25.txt created Dec. 17, 2014 which is approximately 2.75 MB in size. The information in the electronic format of the sequence listing is incorporated herein by reference in its entirety.

FIELD

Certain embodiments are directed to methods and compounds for inhibiting UBE3A-ATS, the endogenous antisense transcript of ubiquitin protein ligase E3A (UBE3A). Such methods and compounds are useful for inducing expression of paternal UBE3A in cells and animals.

BACKGROUND

UBE3A is maternally expressed in neurons and encodes an E3 ubiquitin ligase named E6-AP. An endogenous antisense transcript of UBE3A, termed UBE3A-ATS, has been identified in humans and mice. UBE3A-ATS functions to suppress paternal Ube3a expression. (Meng et al., Hum Mol Genet. 21:3001-12, 2012).

Angelman syndrome (AS) is a neurodevelopmental disorder mostly attributed to deficiency of maternal UBE3A at 15q11.2, whereas paternal UBE3A is subject to genomic imprinting and silencing in neurons. Patients of Angelman syndrome suffer from developmental delay, speech impairment and seizures. Therapies for Angelman syndrome are limited and mainly focus on symptomatic management. (Williams, C. A. et al., Genet. Med., 12: 385-395, 2010).

Recently, topoisomerase inhibitors currently used in cancer treatment were found to "unsilence" paternal Ube3a expression in both a neuronal culture system and mice. (Huang, H. S. et al., Nature, 481: 185-189, 2012). However, the exact mechanism of unsilencing paternal Ube3a expression remains unknown and topoisomerase inhibitors are fraught with safety concerns because they are known to be non-specific and capable of inducing DNA damage, such as single and double-strand breaks.

SUMMARY

Several embodiments provided herein relate to the discovery that antisense compounds targeting UBE3A-ATS induce paternal expression of UBE3A. Several embodiments are drawn to methods and compounds for inducing paternal expression of UBE3A using antisense compounds targeting UBE3A-ATS within an unexpected hotspot located at a region of UBE3A-ATS upstream from the region that overlaps with UBE3A. In certain embodiments, the hotspot is located between an upstream region of UBE3A-ATS that includes the sequence of at least one small nucleolar RNA (snoRNA), such as HBII-52 or MBII-52, and a downstream region of UBE3A-ATS that is complementary to UBE3A (i.e. antisense to UBE3A). Prior to the present discovery manifest in several embodiments described herein, it was uncertain whether UBE3A-ATS could be targeted successfully with antisense compounds and even more unclear where to target within UBE3A-ATS.

The discovery of a hotpot region of UBE3A-ATS described herein was unpredictable in view of several reports teaching that sense transcript expression can be upregulated by targeting antisense transcripts at regions that either overlap or do not overlap with the sense transcripts. For example, on one hand it has been shown that antisense compounds designed to a region of the natural antisense transcript BDNF-AS that overlaps with BDNF increases BDNF mRNA levels. (Madharessi et al., Nat Biotechnol. 30:453-459, 2012). Similar findings have been reported with p21 and Oct4 antisense transcripts (Morris et al., PLoS Genet. 4:e1000258, 2008, Hawkins and Morris, Transcription 1:165-175, 2010). On the other hand, it has been shown that antisense compounds targeting natural antisense transcripts at non-overlapping regions with sense transcripts can upregulate sense transcript expression. (Faghihi et al., PLoS ONE 5:e13177, 2010).

DETAILED DESCRIPTION

Figure 1:
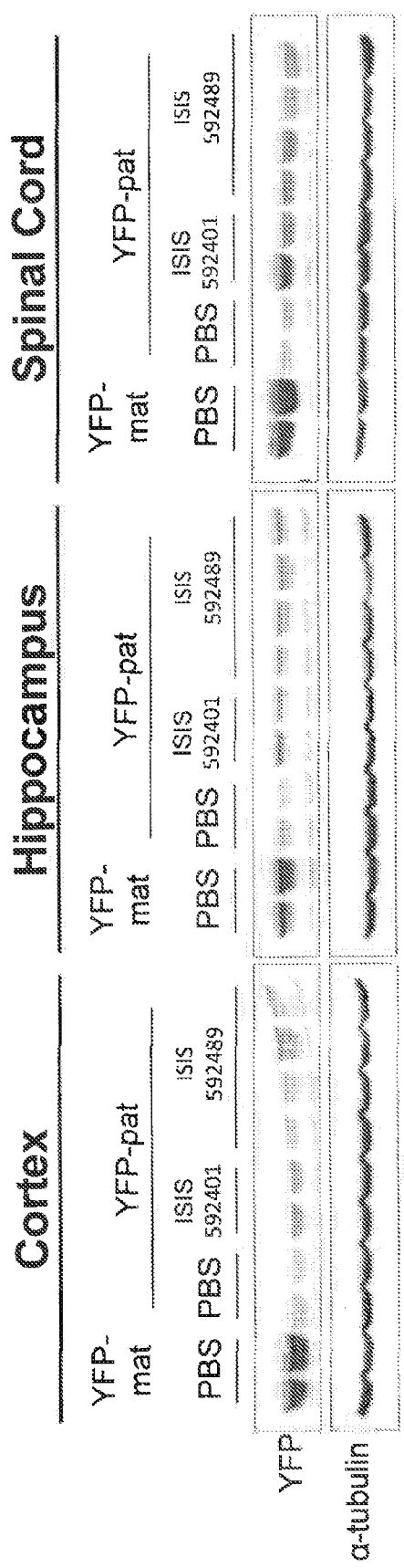
FIG. 1 shows Western Blot analysis using an anti-YFP antibody, which confirmed that treatment with ASO increased paternal Ube3a protein expression.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO described herein is independent of any modification to a sugar moiety, an internucleoside linkage, or a nucleobase.

As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of UBE3A-ATS", it is implied that UBE3A-ATS levels are inhibited within a range of 63% and 77%. Similarly, if it is stated, "the compounds affected at least about 20% induction of paternal UBE3A expression", it is implied that UBE3A levels are induced by a range within 13% and 27%.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Bicyclic nucleic acid" or "BNA" or "BNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

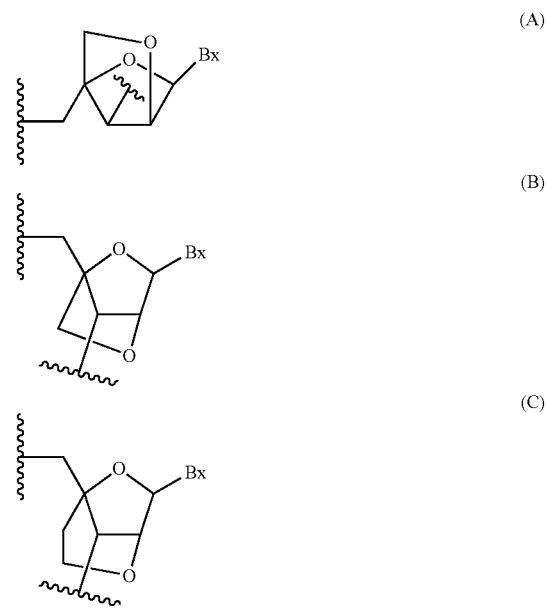

-continued

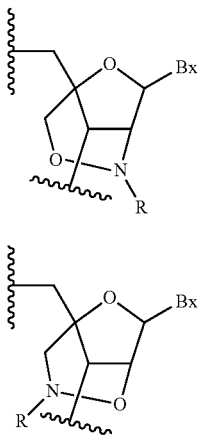

(D)

(E)

As used herein, LNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, O$J_1$, N$J_1J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —[C($R_1$)($R_2$)]$_n$—, —[C($R_1$)($R_2$)]$_n$—O—, —C($R_1R_2$)—N($R_1$)—O— or —C($R_1R_2$)—O—N($R_1$)—. Furthermore, other bridging groups encompassed with the definition of LNA are 4'-$CH_2$-2', 4'-($CH_2$)$_2$-2', 4'-($CH_2$)$_3$-2', 4'-$CH_2$—O-2', 4'-($CH_2$)$_2$—O-2', 4'-$CH_2$—O—N($R_1$)-2' and 4'-$CH_2$—N($R_1$)—O-2'- bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicyclic sugar moiety having an ethylene bridging group in this position, the term ethyleneoxy (4'-$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified motif" refers to an antisense compound comprising a contiguous sequence of nucleosides wherein essentially each nucleoside is a sugar modified nucleoside having uniform modification.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means an antisense compound having a gap segment of 12 or more contiguous 2'-deoxyribonucleotides positioned between 5' and 3' wing segments having from one to six nucleotides having modified sugar moieties.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Peptide" means a molecule formed by linking at least two amino acids by amide bonds. Without limitation, as used herein, "peptide" refers to polypeptides and proteins.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"UBE3A-ATS" and "Ube3a-ATS" can be used interchangeably without capitalization of their spelling referring to any particular species or ortholog.

"UBE3A" and "Ube3A" can be used interchangeably without capitalization of their spelling referring to any particular species or ortholog. Additionally, "UBE3A", "UBE3A", "Ube3A", and "Ube3A" can be used interchangeably without italicization referring to nucleic acid or protein unless specifically indicated to the contrary.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Validated target segment" is defined as at least an 8-nucleobase portion (i.e. 8 consecutive nucleobases) of a target region to which an antisense compound is targeted.

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments are drawn to a method of inducing expression of paternal UBE3A in a cell comprising contacting the cell with an antisense compound targeted to UBE3A-ATS. In several aspects, UBE3A-ATS comprises a nucleic acid sequence at least 85% identical to SEQ ID NO:1 or SEQ ID NO: 2.

Several embodiments provide a method of inducing expression of paternal UBE3A in a cell comprising contacting the cell with an antisense compound targeted to a region of UBE3A-ATS upstream from a region of UBE3A-ATS that is complementary to at least the 3' end of a UBE3A pre-mRNA. Several embodiments provide a method of reducing UBE3A-ATS in a cell comprising contacting the cell with an antisense compound targeted to a region of UBE3A-ATS upstream from a region of UBE3A-ATS complementary to at least the 3' end of a UBE3A pre-mRNA. In some aspects, UBE3A-ATS comprises a nucleic acid sequence at least 85% identical to SEQ ID NO: 1. In the same aspect, the region complementary to at least the 3' end of the UBE3A pre-mRNA can start at nucleobase 1032967 of SEQ ID NO: 1. In another aspect, UBE3A-ATS comprises a nucleic acid sequence at least 85% identical to SEQ ID NO: 2. In the same aspect, the region complementary to at least the 3' end of the UBE3A pre-mRNA can start at nucleobase 513603 of SEQ ID NO: 2. In certain aspects of the foregoing methods, paternal UBE3A expression is induced and/or UBE3A-ATS is reduced in the cell without reducing levels of the neighboring small nucleolar RNAs (snoRNAs) Snrpn, MBII-85/HBII-85, and/or MBII-52/HBII-52, some of are reported to be involved in Prader-Willi syndrome and are deleted in patients suffering from Prader-Willi syndrome (Sahoo, T. et al., Nat. Genet. 2008. 40: 719-21; Tsai, T. et al., Hum. Mol. Genet. 1999. 8: 1357-64).

In several aspects, contacting a cell with an antisense compound targeted to a region of UBE3A-ATS upstream from a region of UBE3A-ATS that is complementary to at least the 3' end of a UBE3A pre-mRNA induces expression of paternal UBE3A and/or reduces UBE3A-ATS in the cell without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Various embodiments are directed to a method of inducing expression of paternal UBE3A in a cell comprising contacting the cell with an antisense compound targeted to a first region of UBE3A-ATS, said first region flanked by (a) an upstream region and (b) a downstream region complementary to at least the 3' end of a UBE3A pre-mRNA. Several embodiments are directed to a method of reducing UBE3A-ATS in a cell comprising contacting the cell with an antisense compound targeted to a first region of UBE3A-ATS, said first region flanked by (a) an upstream region and (b) a downstream region complementary to at least the 3' end of a UBE3A pre-mRNA. In one aspect, the upstream region comprises the sequence of at least one snoRNA. In the same aspect, the snoRNA is HBII-52 or MBII-52. In certain aspects, UBE3A-ATS comprises a nucleic acid sequence at least 85% identical to SEQ ID NO:1 and the first region of UBE3A-ATS consists of nucleobases at least 85% identical to nucleobases 997469 to 1032966 of SEQ ID NO: 1. In several aspects, the UBE3A pre-mRNA comprises a nucleic acid sequence at least 85% identical to SEQ ID NO: 5. In certain aspects, UBE3A-ATS comprises a nucleic acid sequence at least 85% identical to SEQ ID NO:2 and the first region of UBE3A-ATS consists of nucleobases at least 85% identical to nucleobases 446213 through 513602 of SEQ ID NO: 2. In several aspects, the UBE3A pre-mRNA comprises a nucleic acid sequence at least 85% identical to SEQ ID NO: 6. In certain aspects of the foregoing methods, paternal UBE3A expression is induced and/or UBE3A-ATS is reduced in the cell without reducing levels of the neighboring small nucleolar RNAs (snoRNAs) Snrpn, MBII-85/HBII-85, and/or MBII-52/HBII-52. In several aspects, contacting a cell with an antisense compound targeted to a first region of UBE3A-ATS, said first region flanked by (a) an upstream region and (b) a downstream region complementary to at least the 3' end of a UBE3A pre-mRNA, induces expression of paternal UBE3A and/or reduces UBE3A-ATS in the cell without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Certain embodiments relate to a method of inducing expression of paternal UBE3A in a cell comprising contacting the cell with an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO:1. Certain embodiments relate to a method of inhibiting UBE3A-ATS in a cell comprising contacting the cell with an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO: 1. In one aspect, the region complementary to the UBE3A pre-mRNA consists of nucleobases 1032967 to 1110944 of SEQ ID NO:1. In certain aspects of the foregoing methods, paternal UBE3A expression is induced and/or UBE3A-ATS is reduced in the cell without reducing levels of the neighboring small nucleolar RNAs (snoRNAs) Snrpn, MBII-85/HBII-85, and/or MBII-52/HBII-52. In several aspects, contacting a cell with an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO:1, induces expression of paternal UBE3A and/or reduces UBE3A-ATS in the cell without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Certain embodiments relate to a method of inducing expression of paternal UBE3A in a cell comprising contacting the cell with an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2. Certain embodiments relate to a method of inhibiting UBE3A-ATS in a cell comprising contacting the cell with an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO:2. In one aspect, the region complementary to the UBE3A pre-mRNA consists of nucleobases 513603 through 615382 of SEQ ID NO:2. In certain aspects of the foregoing methods, paternal UBE3A expression is induced and/or UBE3A-ATS is reduced in the cell without reducing levels of the neighboring small nucleolar RNAs (snoRNAs) Snrpn, MBII-85/HBII-85, and/or MBII-52/HBII-52. In several aspects, contacting a cell with an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2, induces expression of paternal UBE3A and/or reduces UBE3A-ATS in the cell without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In several aspects of any of the foregoing embodiments, contacting the cell with the antisense compound reduces the level of UBE3A-ATS in the cell and/or induces expression of paternal UBE3A protein in the cell.

In several aspects of any of the foregoing embodiments, the cell is a cultured cell. In the same aspect, the cell is an animal.

Certain embodiments are drawn to a method of inducing expression of paternal UBE3A in an animal comprising administering to the animal an antisense compound targeted to UBE3A-ATS. In several aspects, UBE3A-ATS comprises a nucleic acid sequence at least 85% identical to SEQ ID NO:1 or SEQ ID NO: 2.

Several embodiments relate to a method of inducing expression of paternal UBE3A and/or reducing UBE3A-ATS in an animal comprising administering to the animal an antisense compound targeted to a region of UBE3A-ATS upstream from a region of UBE3A-ATS complementary to at least the 3' end of a UBE3A pre-mRNA. In some aspects, UBE3A-ATS comprises a nucleic acid sequence at least 85% identical to SEQ ID NO:1. In the same aspect, the region complementary to at least the 3' end of the UBE3A pre-mRNA can start at nucleobase 1032967 of SEQ ID NO: 1. In another aspect, UBE3A-ATS comprises a nucleic acid sequence at least 85% identical to SEQ ID NO: 2. In the same aspect, the region complementary to at least the 3' end of the UBE3A pre-mRNA can start at nucleobase 513603 of SEQ ID NO: 2. In certain aspects of the foregoing methods, paternal UBE3A expression is induced and/or UBE3A-ATS is reduced in the animal without reducing levels of the neighboring snoRNAs Snrpn, MBII-85/HBII-85, and/or MBII-52/HBII-52. In several aspects, administering an antisense compound targeted to a region of UBE3A-ATS upstream from a region of UBE3A-ATS that is complementary to at least the 3' end of a UBE3A pre-mRNA induces expression of paternal UBE3A and/or reduces UBE3A-ATS in the animal without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Various embodiments are directed to a method of inducing expression of paternal UBE3A and/or reducing UBE3A-ATS in an animal comprising administering to the animal an antisense compound targeted to a first region of UBE3A-ATS, said first region flanked by (a) an upstream region and (b) a downstream region complementary to a UBE3A pre-mRNA. In one aspect, the upstream region comprises the sequence of least one small nucleolar RNA (snRNA). In the same aspect, the snoRNA is HBII-52 or MBII-52. In certain aspects, UBE3A-ATS comprises a nucleic acid sequence at least 85% identical to SEQ ID NO: 1 and the first region of UBE3A-ATS consists of nucleobases at least 85% identical to nucleobases 997469 to 1032966 of SEQ ID NO: 1. In several aspects, the UBE3A pre-mRNA comprises a nucleic acid sequence at least 85% identical to SEQ ID NO: 5. In certain aspects, UBE3A-ATS comprises a nucleic acid sequence at least 85% identical to SEQ ID NO: 2 and the first region of UBE3A-ATS consists of nucleobases at least 85% identical to nucleobases 446213 through 513602 of SEQ ID NO: 2. In several aspects, the UBE3A pre-mRNA comprises a nucleic acid sequence at least 85% identical to SEQ ID NO: 6. In certain aspects of the foregoing methods, paternal UBE3A expression is induced and/or UBE3A-ATS is reduced in the animal without reducing levels of the neighboring small nucleolar RNAs (snoRNAs) Snrpn, MBII-85/HBII-85, and/or MBII-52/HBII-52. In several aspects, administering an antisense compound targeted to a first region of UBE3A-ATS, said first region flanked by (a) an upstream region and (b) a downstream region complementary to at least the 3' end of a UBE3A pre-mRNA, induces expression of paternal UBE3A and/or reduces UBE3A-ATS in the animal without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Certain embodiments provide a method of inducing expression of paternal UBE3A and/or reducing UBE3A-ATS in an animal comprising administering to the animal an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO: 1. In one aspect, the region complementary to the UBE3A pre-mRNA consists of nucleobases 1032967 to 1110944 of SEQ ID NO: 1. In certain aspects of the foregoing methods, paternal UBE3A expression is induced and/or UBE3A-ATS is reduced in the animal without reducing levels of the neighboring small nucleolar RNAs (snoRNAs) Snrpn, MBII-85/HBII-85, and/or MBII-52/HBII-52. In several aspects, administering an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO:1, induces expression of paternal UBE3A and/or reduces UBE3A-ATS in the animal without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Various embodiments relate to a method of inducing expression of paternal UBE3A and/or reducing UBE3A-ATS in an animal comprising administering to the animal an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2. In one aspect, the region complementary to the UBE3A pre-mRNA consists of nucleobases 513603 through 615382 of SEQ ID NO: 2. In certain aspects of the foregoing methods, paternal UBE3A expression is induced and/or UBE3A-ATS is reduced in the animal without reducing levels of the neighboring small nucleolar RNAs (snoRNAs) Snrpn, MBII-85/HBII-85, and/or MBII-52/HBII-52. In several aspects, administering an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2, induces expression of paternal UBE3A and/or reduces UBE3A-ATS in the animal without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52% 53%, 54% 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In any of the aforementioned embodiments and aspects thereof, the antisense compound can comprise an oligonucleotide consisting of 12 to 30 linked nucleosides, wherein the oligonucleotide is at least 85% complementary to a UBE3A-ATS nucleic acid sequence. In certain aspects, the oligonucleotide is at least 90%, at least 95%, or 100% complementary over its entire length to an equal length region of a UBE3A-ATS nucleic acid sequence. In certain aspects, the antisense compound or oligonucleotide is a single-stranded oligonucleotide. In several aspects, the oligonucleotide is a modified oligonucleotide. In the same aspect, the modified oligonucleotide can comprise at least one modified internucleoside linkage. Yet again in the same aspect, the modified internucleoside linkage can be a phosphorothioate internucleoside linkage. In several aspects, at least one nucleoside comprises a modified sugar. In the same aspect, the modified sugar is a bicyclic sugar comprising a bridge between the 4' and the 2' positions of the sugar, such as a bridge is selected from 4'-CH(CH$_3$)—O-2', 4'-CH$_2$-2', 4'-(CH$_2$)$_2$-2', 4'-CH$_2$—O-2', 4'-(CH$_2$)$_2$—O-2', 4'-CH$_2$—O—N(R$_1$)-2' and 4'-CH2-N(R$_1$)—O-2'- wherein each R1 is, independently, H, a protecting group or C1-C12 alkyl. Further in the same aspect, the bridge is 4'-CH(CH$_3$)—O-2'.

In any of the preceding embodiments and aspects thereof including a modified sugar, the modified sugar can comprise a 2'-O-methoxyethyl group.

In any of the preceding embodiments and aspects thereof including a modified oligonucleotide, at least one nucleoside can comprise a modified nucleobase, such as a 5-methylcytosine.

In any of the foregoing embodiments and aspects thereof, the antisense compound or modified oligonucleotide induces expression of paternal UBE3A by at least 20%, at least 30%, at least 40%., at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least 250%.

Certain embodiments are drawn to a method of treating an animal with an antisense compound targeted to UBE3A-ATS comprising selecting an animal in need thereof and administering to the animal an antisense compound targeted to UBE3A-ATS. In several aspects, UBE3A-ATS comprises a nucleic acid sequence at least 85% identical to SEQ ID NO: 1 or SEQ ID NO: 2.

Several embodiments are directed to a method of treating an animal with an antisense compound targeted to UBE3A-ATS comprising selecting an animal in need thereof and administering to the animal an antisense compound targeted to a region of UBE3A-ATS upstream from a region of UBE3A-ATS complementary to at least the 3' end of a UBE3A pre-mRNA. In some aspects, UBE3A-ATS comprises a nucleic acid sequence at least 85% identical to SEQ ID NO: 1. In the same aspect, the region complementary to at least the 3' end of the UBE3A pre-mRNA can start at nucleobase 1032967 of SEQ ID NO: 1. In another aspect, UBE3A-ATS comprises a nucleic acid sequence at least 85% identical to SEQ ID NO: 2. In the same aspect, the region complementary to at least the 3' end of the UBE3A pre-mRNA can start at nucleobase 513603 of SEQ ID NO: 2.

Various embodiments relate to a method of treating an animal with an antisense compound targeted to UBE3A-ATS comprising selecting an animal in need thereof and administering to the animal an antisense compound targeted to a first region of UBE3A-ATS, said first region flanked by (a) an upstream region and (b) a downstream region complementary to at least the 3' end of a UBE3A pre-mRNA. In one aspect, the upstream region comprises the sequence of at least one small nucleolar RNAs (snoRNA). In the same aspect, the snoRNA is HBII-52 or MBII-52. In certain aspects, UBE3A-ATS comprises a nucleic acid sequence at least 85% identical to SEQ ID NO: 1 and the first region of UBE3A-ATS consists of nucleobases at least 85% identical to nucleobases 997469 to 1032966 of SEQ ID NO: 1. In several aspects, the UBE3A pre-mRNA comprises a nucleic acid sequence at least 85% identical to SEQ ID NO: 5. In certain aspects, UBE3A-ATS comprises a nucleic acid sequence at least 85% identical to SEQ ID NO:2 and the first region of UBE3A-ATS consists of nucleobases at least 85% identical to nucleobases 446213 through 513602 of SEQ ID NO: 2. In several aspects, the UBE3A pre-mRNA comprises a nucleic acid sequence at least 85% identical to SEQ ID NO: 6.

Certain embodiments provide a method of treating an animal with an antisense compound targeted to UBE3A-ATS comprising selecting an animal in need thereof and administering to the animal an antisense compound targeted to UBE3A-ATS within 35498 nucleobases upstream from the start of the region complementary to a UBE3A pre-mRNA, wherein UBE3A-ATS comprises a nucleic acid sequence at least 85% identical to the sequence of SEQ ID NO: 1. In one aspect, the region complementary to the UBE3A pre-mRNA consists of nucleobases 1032967 to 1110944 of SEQ ID NO: 1.

Several embodiments relate to a method of treating an animal with an antisense compound targeted to UBE3A-ATS comprising selecting an animal in need thereof and administering to the animal an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2. In one aspect, the region complementary to the UBE3A pre-mRNA consists of nucleobases 513603 through 615382 of SEQ ID NO: 2.

In certain aspects of any of the foregoing embodiments drawn to a method of treating an animal, the animal has Angelman Syndrome. In certain aspects, the animal having Angelman Syndrome treated according to the methods provided herein show an improvement in anxiety, learning, balance, motor function, and/or seizures.

In certain aspects of any of the foregoing embodiments drawn to a method of treating an animal, administering an antisense compound provided treats the animal without reducing levels of the neighboring small nucleolar RNAs (snoRNAs) Snrpn, MBII-85/HBII-85, and/or MBII-52/HBII-52. In several aspects, administering an antisense compound provided herein treats the animal without reducing Snrpn, MBII-85/HBII-85, and/or MBII-52/HBII-52 levels by more than about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Certain embodiments are drawn to an antisense compound targeted to UBE3A-ATS. In several aspects, UBE3A-

ATS comprises a nucleic acid sequence at least 85% identical to SEQ ID NO: 1 or SEQ ID NO: 2.

Several embodiments provide an antisense compound targeted to a region of UBE3A-ATS upstream from a region of UBE3A-ATS complementary to at least the 3' end of a UBE3A pre-mRNA. In some aspects, UBE3A-ATS comprises a nucleic acid sequence at least 85% identical to SEQ ID NO: 1. In the same aspect, the region complementary to at least the 3' end of the UBE3A pre-mRNA can start at nucleobase 1032967 of SEQ ID NO: 1. In another aspect, UBE3A-ATS comprises a nucleic acid sequence at least 85% identical to SEQ ID NO: 2. In the same aspect, the region complementary to at least the 3' end of the UBE3A pre-mRNA can start at nucleobase 513603 of SEQ ID NO: 2.

Various embodiments are directed to an antisense compound targeted to a first region of UBE3A-ATS, said first region flanked by (a) an upstream region and (b) a downstream region complementary to at least the 3' end of a UBE3A pre-mRNA. In one aspect, the upstream region comprises the sequence of at least one small nucleolar RNAs (snoRNA). In the same aspect, the snoRNA is HBII-52 or MBII-52. In certain aspects, UBE3A-ATS comprises a nucleic acid sequence at least 85% identical to SEQ ID NO: 1 and the first region of UBE3A-ATS consists of nucleobases at least 85% identical to nucleobases 997469 to 1032966 of SEQ ID NO: 1. In several aspects, the UBE3A pre-mRNA comprises a nucleic acid sequence at least 85% identical to SEQ ID NO: 5. In certain aspects, UBE3A-ATS comprises a nucleic acid sequence at least 85% identical to SEQ ID NO: 2 and the first region of UBE3A-ATS consists of nucleobases at least 85% identical to nucleobases 446213 through 513602 of SEQ ID NO: 2. In several aspects, the UBE3A pre-mRNA comprises a nucleic acid sequence at least 85% identical to SEQ ID NO: 6.

Certain embodiments relate to an antisense compound targeted to UBE3A-ATS within 35498 nucleobases upstream from the start of a region complementary to the UBE3A pre-mRNA, wherein UBE3A-ATS comprises a nucleic acid sequence at least 85% identical to the sequence of SEQ ID NO: 1. In one aspect, the region complementary to the UBE3A pre-mRNA consists of nucleobases 1032967 to 1110944 of SEQ ID NO: 1.

Certain embodiments relate to an antisense compound targeted to UBE3A-ATS within 67390 nucleobases upstream from the start of a region complementary to the UBE3A pre-mRNA, wherein UBE3A-ATS comprises a nucleic acid sequence at least 85% identical to the sequence of SEQ ID NO: 2. In one aspect, the region complementary to the UBE3A pre-mRNA consists of nucleobases 513603 through 615382 of SEQ ID NO: 2.

In several aspects of any of the foregoing embodiments, the antisense compound is capable of reducing the level of UBE3A-ATS in the cell and/or inducing expression of paternal UBE3A protein in the cell.

In any of the aforementioned embodiments and aspects thereof, the antisense compound can comprise an oligonucleotide consisting of 12 to 30 linked nucleosides, wherein the oligonucleotide is at least 85% complementary to a UBE3A-ATS nucleic acid sequence. In certain aspects, the oligonucleotide is at least 90%, at least 95%, or 100% complementary over its entire length to an equal length region of a UBE3A-ATS nucleic acid sequence. In certain aspects, the antisense compound or oligonucleotide is a single-stranded oligonucleotide. In several aspects, the oligonucleotide is a modified oligonucleotide. In the same aspect, the modified oligonucleotide can comprise at least one modified internucleoside linkage. Yet again in the same aspect, the modified internucleoside linkage can be a phosphorothioate internucleoside linkage. In several aspects, at least one nucleoside comprises a modified sugar. In the same aspect, the modified sugar is a bicyclic sugar comprising a bridge between the 4' and the 2' positions of the sugar, such as a bridge is selected from 4'-CH(CH$_3$)—O-2', 4'-CH$_2$-2', 4'-(CH$_2$)$_2$-2', 4'-CH$_2$—O-2', 4'-(CH$_2$)$_2$—O-2', 4'-CH$_2$—O—N(R$_1$)-2' and 4'-CH2-N(R$_1$)—O-2'- wherein each R1 is, independently, H, a protecting group or C1-C12 alkyl. Further in the same aspect, the bridge is 4'-CH(CH$_3$)—O-2'.

In any of the preceding embodiments and aspects thereof including a modified sugar, the modified sugar can comprise a 2'-O-methoxyethyl group.

In any of the preceding embodiments and aspects thereof including a modified oligonucleotide, at least one nucleoside can comprise a modified nucleobase, such as a 5-methylcytosine.

In any of the foregoing embodiments and aspects thereof, the antisense compound or modified oligonucleotide is capable of inducing expression of paternal UBE3A by at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least 250%.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to a UBE3A-ATS nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a UBE3A-ATS nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows:

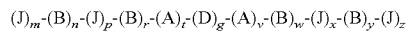

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

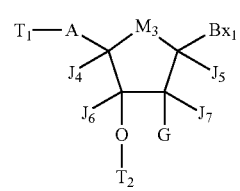

wherein:
T$_1$ is an optionally protected phosphorus moiety;
T$_2$ is an internucleoside linking group linking the compound of Formula IIc to the oligomeric compound;
A has one of the formulas:

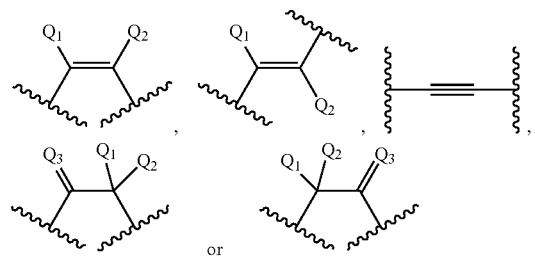

Q$_1$ and Q$_2$ are each, independently, H, halogen, C$_1$-C$_6$ alkyl, substituted C$_1$-C$_6$ alkyl, C$_1$-C$_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

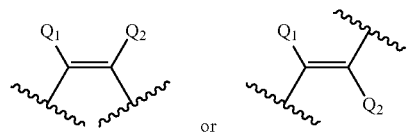

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

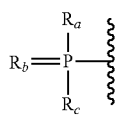

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—C$(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—C$(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

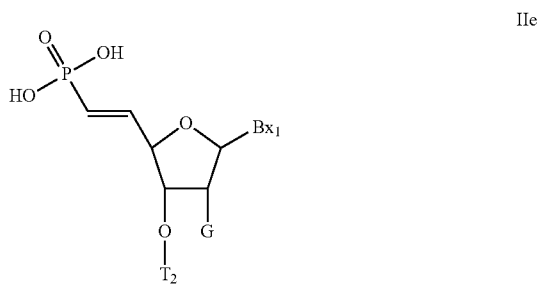

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif.

Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

$-(A)_2-(B)_x-(A)_2-(C)_y-(A)_3-$ wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$5'-(Q)-(AB)_xA_y-(D)_z$ wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:

$5'-(Q)-(A)_x-(D)_z$ wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is UBE3A-ATS. In certain embodiment, the degradation of the targeted UBE3A-ATS is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target UBE3A-ATS by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxyribonucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

In certain embodiments, the UBE3A-ATS nucleic acid comprises the sequence set forth in the complement of GENBANK Accession No. NT_187035.1 truncated from nucleotides 66484120 to 67595063 (incorporated herein as SEQ ID NO: 1) or the sequence set forth in GENBANK Accession No. NT_026446.14 truncated from nucleotides 25068794 to 25684175 (incorporated herein as SEQ ID NO: 2). SEQ ID NO: 1 provides sequence from chromosome 7 of the mouse genome and SEQ ID NO: 2 provides sequence from chromosome 15 of the human genome. The mouse and human genomic loci corresponding to these SEQ ID NOs share a highly conserved genomic organization that includes a Snrpn gene, snoRNAs, and UBE3A-ATS in the same structural arrangement along their syntenic chromosomes. In addition to the highly conserved genomic map of the mouse and human syntenic loci, the genomic imprinting mechanism is also conserved at this loci; in mice and humans, most neurons express Ube3a only from the maternally-inherited allele. (Huang, H. S. et al., Nature, 481: 185-189, 2012)

In certain embodiments, UBE3A-ATS comprises a nucleic acid sequence at least 85%, at least 90%, at least 95%, or 100% identical to the complement of GENBANK Accession No. NT_187035.1 truncated from nucleotides 66484120 to 67595063 (incorporated herein as SEQ ID NO: 1) or GENBANK Accession No. NT_026446.14 truncated from nucleotides 25068794 to 25684175 (incorporated herein as SEQ ID NO: 2). In certain embodiments, UBE3A comprises a nucleic acid sequence at least 85%, at least 90%, at least 95%, or 100% identical to the reverse complement of nucleotides 1032967 to 1110944 of SEQ ID NO: 1 (incorporated herein as SEQ ID NO: 5) or the reverse complement of nucleotides 513603 to 615382 of SEQ ID NO: 2 (incorporated herein as SEQ ID NO: 6).

Targeting includes determination of at least one target segment to which an antisense compound hybridizes, such that a desired effect occurs. In certain embodiments, the desired effect is a reduction in UBE3A-ATS nucleic acid levels. In certain embodiments, the desired effect is induced expression of paternal UBE3A.

In certain embodiments, antisense compounds are targeted to UBE3A-ATS, which comprises a nucleic acid sequence at least 85%, at least 90%, at least 95%, or 100% identical to the complement of GENBANK Accession No. NT_187035.1 truncated from nucleotides 66484120 to 67595063 (incorporated herein as SEQ ID NO: 1) or GENBANK Accession No. NT_026446.14 truncated from nucleotides 25068794 to 25684175 (incorporated herein as SEQ ID NO: 2). In certain aspects, antisense compounds are targeted to a region of UBE3A-ATS upstream from the region of UBE3A-ATS complementary to at least the 3' end of a UBE3A pre-mRNA. Stated differently, in certain aspects antisense compounds are targeted to a region of UBE3A-ATS that is upstream from the region of UBE3A-ATS overlapping or antisense to UBE3A. For example, the region of UBE3A-ATS complementary to at least the 3' end of the UBE3A pre-mRNA can start at nucleobase 1032967 of SEQ ID NO: 1 or nucleobase 513603 of SEQ ID NO: 2. In certain aspects, the region of UBE3A-ATS complementary to at least the 3' end of the UBE3A pre-mRNA can consist of nucleobases 1032967 to 1110944 of SEQ ID NO: 1 or nucleobases 513603 to 615382 of SEQ ID NO: 2.

In certain embodiments, antisense compounds are targeted to a first region of UBE3A-ATS that is flanked by (a) an upstream region and (b) a downstream region complementary to at least the 3' end of a UBE3A pre-mRNA. Stated differently, in certain embodiments, antisense compounds are targeted to a first region of UBE3A-ATS that is flanked by (a) an upstream region and (b) a downstream region that overlaps or is antisense to UBE3A. In certain embodiments, the first region can consist of a nucleotide sequence at least 85%, at least 90%, at least 95%, or 100% identical to nucleobases 997469 to 1032966 of SEQ ID NO: 1 (the complement of GENBANK Accession No. NT_187035.1 truncated from nucleotides 66484120 to 67595063). In certain embodiments, the first region can consist of a nucleotide sequence at least 85%, at least 90%, at least 95, or 100% identical to nucleobases 446213 to 513602 of SEQ ID NO: 2 (GENBANK Accession No. NT_026446.14 truncated from nucleotides 25068794 to 25684175). In certain aspects, the downstream region complementary to at least the 3' end of the UBE3A pre-mRNA can consist of nucleobases 1032967 to 1110944 of SEQ ID NO: 1 or nucleobases 513603 to 615382 of SEQ ID NO: 2.

In certain embodiments, antisense compounds are targeted to UBE3A-ATS within 35498 nucleobases upstream from the start of a region complementary to at least the 3' end of the UBE3A pre-mRNA, wherein UBE3A-ATS comprises a nucleic acid sequence at least 85%, at least 90%, at least 95%, or 100% identical to the complement of GENBANK Accession No. NT_187035.1 truncated from nucleotides 66484120 to 67595063 (incorporated herein as SEQ ID NO: 1). In certain aspects, the region complementary to at least the 3' end the UBE3A pre-mRNA consists of nucleobases 1032967 to 1110944 of SEQ ID NO: 1. In certain embodiments antisense compounds are targeted to UBE3A-ATS within 35498 nucleobases upstream from the region of UBE3A-ATS (SEQ ID NO:1) overlapping or antisense to UBE3A.

In certain embodiments, antisense compounds are targeted to UBE3A-ATS within 67390 nucleobases upstream from the start of a region complementary to the UBE3A pre-mRNA, wherein UBE3A-ATS comprises a nucleic acid sequence at least 85%, at least 90%, at least 95%, or 100% identical to GENBANK Accession No. NT_026446.14 truncated from nucleotides 25068794 to 25684175. In certain aspects, the region complementary to the UBE3A pre-mRNA consists of nucleobases 513603 through 615382 of SEQ ID NO: 2. In certain embodiments, antisense compounds are targeted to UBE3A-ATS within 67390 nucleobases upstream from the region of UBE3A-ATS (SEQ ID NO: 2) overlapping or antisense to UBE3A.

In certain embodiments, antisense compounds target UBE3A-ATS immediately downstream of HBII-52 or MBII-52 snoRNA to the region overlapping or antisense to UBE3A. In several aspects, such antisense compounds target UBE3A-ATS between nucleobases 1 to 35499 of SEQ ID NO: 3. In several aspects, such antisense compounds target UBE3A-ATS between nucleobases 1 to 67391 of SEQ ID NO: 4.

There may be variation in activity (e.g., as defined by percent reduction of UBE3A-ATS nucleic acid levels or percent induction of paternal UBE3A expression) of the antisense compounds within an active target region. In certain embodiments, an induction of paternal UBE3A expression is indicative of inhibition of UBE3A-ATS expression.

Hybridization

In some embodiments, hybridization occurs between an antisense compound disclosed herein and an UBE3A-ATS. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with UBE3A-ATS.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a UBE3A-ATS nucleic acid).

Non-complementary nucleobases between an antisense compound and a UBE3A-ATS nucleic acid may be tolerated provided that the antisense compound remains able to specifically hybridize to a target nucleic acid. Moreover, an antisense compound may hybridize over one or more segments of a UBE3A-ATS nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a UBE3A-ATS nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a UBE3A-ATS nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a UBE3A-ATS nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a UBE3A-ATS nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a UBE3A-ATS nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C($R_1$)($R_2$) (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' (also referred to as constrained ethyl or cEt) and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C—(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

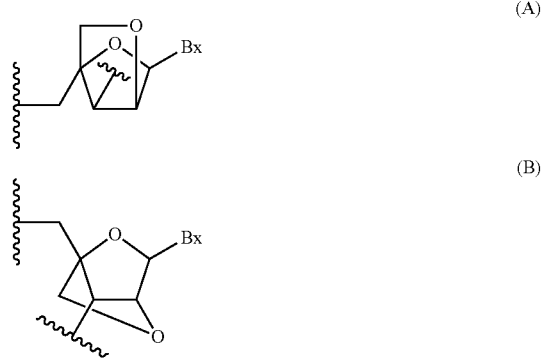

(C) 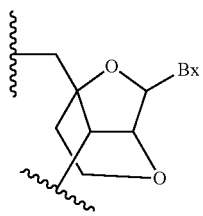

(D) 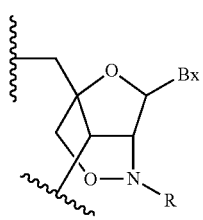

(E) 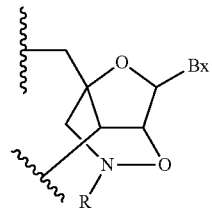

(F) 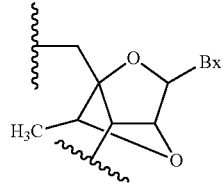

(G) 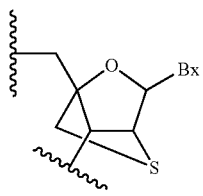

(H) 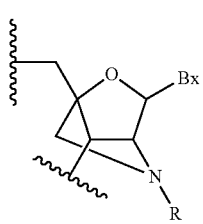

(I) 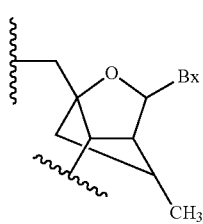

(J) 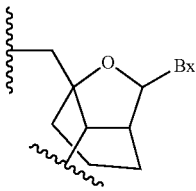

(K) 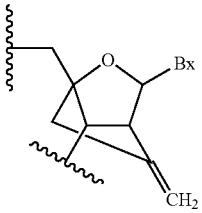

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

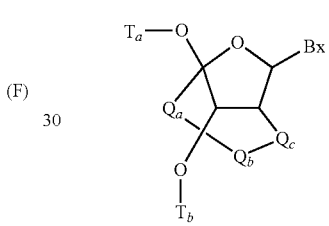

I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

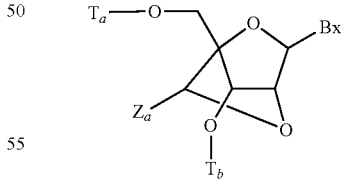

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

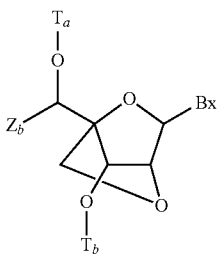

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

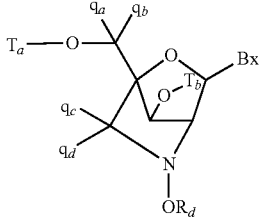

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

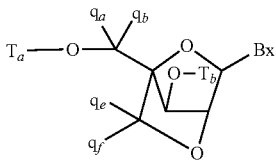

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O) $NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

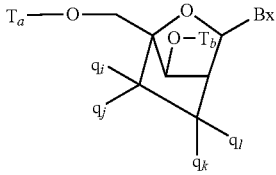

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$—NH$_2$, O(CH$_2$)$_n$—CH$_3$, O(CH$_2$)$_n$—F, O(CH$_2$)$_n$—ONH$_2$, OCH$_2$C(=O)N(H)CH$_3$, and O(CH$_2$)$_n$ON[(CH$_2$)$_n$—CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), mannitol nucleic acid (MNA) (see Leumann, *Bioorg. Med. Chem.*, 2002, 10, 841-854) or fluoro HNA (F-HNA) having a tetrahydropyran ring system as illustrated below:

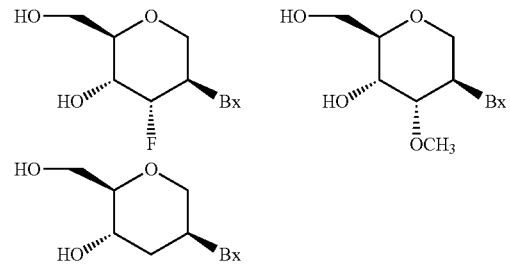

In certain embodiments, sugar surrogates are selected having Formula VII:

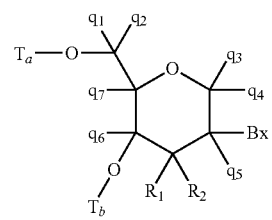

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166, 315; 5,185,444; and 5,034,506). As used here, the term "morpholino" means a sugar surrogate having the following formula:

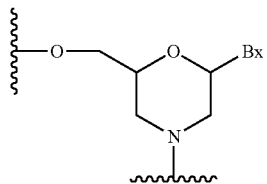

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

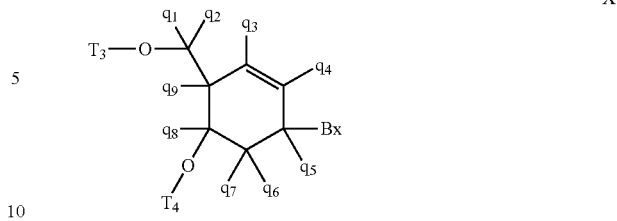

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N(R$_m$)(R$_n$), where each R$_m$ and R$_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118, 800; 5,319,080; 5,359,044; 5,393,878; 5,446,137; 5,466, 786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to UBE3A-ATS comprise one or more modified nucleobases. In certain embodiments, shortened or gap-widened antisense oligonucleotides targeted to UBE3A-ATS comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

For additional conjugates including those useful for ssRNA and their placement within antisense compounds, see e.g., U.S. Application No. 61/583,963.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of the Antisense Sequence of Ubiquitin Protein Ligase E3A (Ube3a-ATS) in Primary Neuronal Cells Antisense oligonucleotides were designed targeting the mouse sequence immediately downstream of MBII-52 snoRNA to the beginning of Ube3a antisense sequence, described herein as nucleotides 997469 to 1110944 of SEQ ID NO: 1 and were tested for their effects on up-regulating the expression of the paternal allele of Ube3a in vitro.

The newly designed chimeric antisense oligonucleotides in Table 1 were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

Primary cultures of hippocampal and cortical neurons were obtained from P0-P2 Ube3a+/YFP offspring of C57BL/6 female mice crossed to Ube3a-YFP male mice (Dindot, S. V. et al., Hum. Mol. Genet. 2008. 17: 111-118). Chopped cortical hemispheres were digested with 0.25% trypsin and mechanically dissociated. Neurons were cultured in a Neurobasal Medium (Invitrogen, Carlsbad, Calif.) supplemented with B27 (Invitrogen) on plates coated with poly-D-lysine (Sigma-Aldrich, St Louis, Mo.). Half of the medium was changed at day 4 and the culture was further maintained for 3 more days at 37° C. in 5% $CO_2$. Sets of cell culture were treated with antisense oligonucleotides by free uptake at a final concentration of 15 μM in the presence of Ara-C to inhibit glial proliferation. A set of cells treated with PBS was used as the untreated control.

Three days after antisense oligonucleotide treatment, cells were fixed with 4% paraformaldehyde for 1 hr. The cells were then washed three times with PBS, and blocked with 5% goat serum (Sigma-Aldrich, St Louis, Mo.) for 1 hr at room temperature. The cells were co-stained with anti-GFP (NB600-308, Novus Biologicals, Littleton, Colo.) at 1:2,500 dilution and anti-NeuN (MAB377, Millipore, Billerica, Mass.) at 1:500 dilution at 4° C. overnight in a humidified chamber with gentle agitation. After three washed in 0.5% Tween-20 in PBS, the cells were stained with secondary goat anti-rabbit antibody conjugated with Alexa Fluor 488 or goat anti-mouse antibody conjugated with Alexa Fluor 555 (Invitrogen, Carlsbad, Calif.) both at 1:1000 dilution. After washes, the plates were imaged with Texas Red and FITC channel by ImageXpress$^{Ultra}$ confocal system (Molecular Device) with a 20× objective. The laser power was manually set for each plate to avoid fluorescence saturation in the samples. Nine images were taken from each well. The images were then processed with the MetaXpress software (Molecular Device) to quantify FITC intensity in those Texas Red positive cells. Typically 200-800 cells were scored per well and the signal intensity was averaged, and normalized to untransfected control cells.

Forty-three antisense oligonucleotides targeting unique sites within the region antisense to the Ube3a pre-mRNA at nucleotides 1032967 to 1110944 of SEQ ID NO: 1) were tested for their effect on inducing expression of Ube3a protein, as quantified by fluorescence. The average induction of the protein after treatment with these ASOs was 18% over the untreated control. A hundred and seventy six oligonucleotides targeting unique sites within the nucleotide region immediately downstream of MBII-52 snoRNA and upstream of the region antisense to the Ube3a pre-mRNA (nucleotides 997469 to 1032966 of SEQ ID NO: 1), designated in the Tables as the 'hotspot', were also tested for their effect on inducing expression of Ube3a-YFP protein. The average induction of the protein after treatment with these ASOs was 83% over the untreated control. The results of the complete screening of the antisense oligonucleotides are presented in Tables 1-3; each Table represents each screening plate utilized. '% induction' is expressed as the percent induction of the protein over the untreated control. "Target start site" indicates the 5'-most nucleotide to which the gapmer is targeted on SEQ ID NO: 1. "Target stop site" indicates the 3'-most nucleotide to which the gapmer is targeted on SEQ ID NO: 1.

TABLE 1

| Target Start Site | Target Stop Site | Region | Sequence | ISIS No | % upregulation | SEQ ID NO |
|---|---|---|---|---|---|---|
| 1003255 | 1003274 | hotspot | GTTATACACACATATATTTT | 592429 | 0 | 7 |
| 1003431 | 1003450 | hotspot | TAGCTTAAACACACTTTTTC | 592430 | 25 | 8 |
| 1003601 | 1003620 | hotspot | ATATGTTGGTCAGCTACTAC | 592431 | 81 | 9 |
| 1003801 | 1003820 | hotspot | GTATATCCTTCCAGATCCTT | 592432 | 157 | 10 |
| 1003971 | 1003990 | hotspot | TGAGTTCATTGGCACATTCA | 592433 | 102 | 11 |
| 1004144 | 1004163 | hotspot | CTAGAAGGTGATATGAGGAT | 592434 | 59 | 12 |
| 1004318 | 1004337 | hotspot | ATAAATATTTCTGCATATTG | 592435 | 2 | 13 |
| 1004488 | 1004507 | hotspot | CATGTACATCCCTATACCTG | 592436 | 126 | 14 |
| 1004658 | 1004677 | hotspot | GACACTTTTCTTGCATAAAT | 592437 | 67 | 15 |
| 1004833 | 1004852 | hotspot | GTCAAAATAGTTATTTTGGG | 592438 | 38 | 16 |
| 1005007 | 1005026 | hotspot | AAAATTTTTATCTCAGCTAC | 592439 | 4 | 17 |
| 1005178 | 1005197 | hotspot | TAAGAAGTAAGCAACTAGGG | 592440 | 54 | 18 |
| 1005348 | 1005367 | hotspot | AGCACATGCAATGATTAGAT | 592441 | 95 | 19 |
| 1005518 | 1005537 | hotspot | ACAATATATATTTTGAAACT | 592442 | 0 | 20 |
| 1005688 | 1005707 | hotspot | CAAGATGGAGAATTCTTGGC | 592443 | 9 | 21 |
| 1005858 | 1005877 | hotspot | TGAATATGCTTGACCCATAG | 592444 | 161 | 22 |
| 1006028 | 1006047 | hotspot | TTCCTTTGTGTAAATGTACC | 592445 | 72 | 23 |
| 1006245 | 1006264 | hotspot | TCAAGCATACTTGGGCCTTC | 592446 | 135 | 24 |
| 1006420 | 1006439 | hotspot | AACACCTGGCAGCTGCATAC | 592447 | 97 | 25 |
| 1006590 | 1006609 | hotspot | TGTTAGTGTCCCTATCCGTC | 592448 | 158 | 26 |
| 1006760 | 1006779 | hotspot | CTGCAAGAACAGCATAGCAT | 592449 | 89 | 27 |
| 1006930 | 1006949 | hotspot | CAAAGGTCCAGGTTAGTTGA | 592450 | 41 | 28 |
| 1007104 | 1007123 | hotspot | TTTCAGGCCCCACCCTCGGG | 592451 | 73 | 29 |
| 1007275 | 1007294 | hotspot | AGGTCCAACATCTTTCTTTC | 592452 | 140 | 30 |
| 1007483 | 1007502 | hotspot | AATATGCTGGTCAAGCCTTC | 592453 | 97 | 31 |
| 1007699 | 1007718 | hotspot | AATGCAGTTTGCTATGGCTC | 592454 | 110 | 32 |
| 1007869 | 1007888 | hotspot | GGTTGTGAGCAACCATGTGG | 592455 | 92 | 33 |
| 1008047 | 1008066 | hotspot | ATTATATGATTGCATTTGAA | 592456 | 12 | 34 |
| 1008230 | 1008249 | hotspot | CATAGATGTTAAATTGTTAA | 592457 | 0 | 35 |
| 1008581 | 1008600 | hotspot | ATGTGATCTTTTAAGATGTA | 592459 | 13 | 36 |
| 1008751 | 1008770 | hotspot | CATGAACAGTTATTCATTAT | 592460 | 32 | 37 |
| 1009091 | 1009110 | hotspot | GCTATTTTCCTAGGAGCATT | 592461 | 68 | 38 |

TABLE 1-continued

| Target Start Site | Target Stop Site | Region | Sequence | ISIS No | % upregulation | SEQ ID NO |
|---|---|---|---|---|---|---|
| 1009262 | 1009281 | hotspot | GAAGTGTTTTAAGGTTTTCA | 592462 | 0 | 39 |
| 1009604 | 1009623 | hotspot | AACCCAGTAATACTGAGCGC | 592464 | 92 | 40 |
| 1009790 | 1009809 | hotspot | TGGATCCTCAGGTGCGACTC | 592465 | 80 | 41 |
| 1010033 | 1010052 | hotspot | GTACTGGTTAATTAATATTG | 592466 | 6 | 42 |
| 1010298 | 1010317 | hotspot | ATTTCAAGTGTTATCCCCTT | 592467 | 192 | 43 |
| 1010468 | 1010487 | hotspot | TATTGAAAATGTGAATCACT | 592468 | 31 | 44 |
| 1010638 | 1010657 | hotspot | GTTTTATCAGAATGGCTCTA | 592469 | 138 | 45 |
| 1010808 | 1010827 | hotspot | CACCATTTATTAAAGATGTT | 592470 | 36 | 46 |
| 1010978 | 1010997 | hotspot | CCTGCAGAGGTATCTGAACC | 592471 | 70 | 47 |
| 1011152 | 1011171 | hotspot | TTAAATAAAGCCTTTATTAA | 592472 | 1 | 48 |
| 1011331 | 1011350 | hotspot | TGAAACAGCTGAGCAATCTC | 592473 | 108 | 49 |
| 1011707 | 1011726 | hotspot | TTTAACCACAATTGTTCTGG | 592475 | 84 | 50 |
| 1011877 | 1011896 | hotspot | TAGAGGTAGCCTTTCTGATG | 592476 | 132 | 51 |
| 1012050 | 1012069 | hotspot | AGTCCCAGAGATCCTACCTG | 592477 | 117 | 52 |
| 1012220 | 1012239 | hotspot | GTGTGTGCAAATGGAGGCTA | 592478 | 55 | 53 |
| 1012404 | 1012423 | hotspot | ATGGTAGTTGTAATTTTCGG | 592479 | 93 | 54 |
| 1012579 | 1012598 | hotspot | AAATGTGATCATTTTACTCT | 592480 | 50 | 55 |
| 1012751 | 1012770 | hotspot | GTTCTACTTTAATCACATTC | 592481 | 114 | 56 |
| 1012921 | 1012940 | hotspot | GTAGTTGTCTTCAGACAAAT | 592482 | 215 | 57 |
| 1013122 | 1013141 | hotspot | TGTTTACATCCCCAAATCTG | 592483 | 191 | 58 |
| 1013292 | 1013311 | hotspot | GTGTAATGTGTGGCTGACTT | 592484 | 153 | 59 |
| 1013488 | 1013507 | hotspot | GTGTATATGCTAGCTTGTGC | 592485 | 132 | 60 |
| 1013658 | 1013677 | hotspot | TACCCATTCCTTGATCAATT | 592486 | 138 | 61 |
| 1013857 | 1013876 | hotspot | TGTAGATAAAGAAATTATCT | 592487 | 0 | 62 |
| 1014197 | 1014216 | hotspot | AGCCAACATTGTTTAACCAG | 592488 | 180 | 63 |
| 1014367 | 1014386 | hotspot | TTGCCAGGCTTGTGCCAGAT | 592489 | 196 | 64 |
| 1014538 | 1014557 | hotspot | AATAATATCTACTTGTGTCC | 592490 | 80 | 65 |
| 1014708 | 1014727 | hotspot | ATCCAATTTCTAGTTGAATC | 592491 | 141 | 66 |
| 1014878 | 1014897 | hotspot | TACTTAAGTGATGTCACTGA | 592492 | 132 | 67 |
| 1015048 | 1015067 | hotspot | TAATCTTGTGATATGGTATG | 592493 | 101 | 68 |
| 1015218 | 1015237 | hotspot | GAGTGAAAATCAGTCTAACT | 592494 | 76 | 69 |
| 1015546 | 1015565 | hotspot | GAGATTTTAGGATGTGTTTC | 592495 | 40 | 70 |
| 1015716 | 1015735 | hotspot | ACACTACTTTAGAGTGCACA | 592496 | 181 | 71 |
| 1015911 | 1015930 | hotspot | ATTCTTTAAAATGTGAACTG | 592497 | 28 | 72 |
| 1016081 | 1016100 | hotspot | ATATCATCAAGGAAAATGTT | 592498 | 14 | 73 |
| 1016262 | 1016281 | hotspot | ATTAAATCCTAGGTTTGCTC | 592499 | 68 | 74 |
| 1016432 | 1016451 | hotspot | CTGCCAACCAAGAATTACTA | 592500 | 158 | 75 |
| 1016602 | 1016621 | hotspot | AAGACATGGCTACAGACAAC | 592501 | 177 | 76 |
| 1016772 | 1016791 | hotspot | GAGGAAACAGTTGTTATGAC | 592502 | 53 | 77 |

TABLE 1-continued

| Target Start Site | Target Stop Site | Region | Sequence | ISIS No | % upregulation | SEQ ID NO |
|---|---|---|---|---|---|---|
| 1017123 | 1017142 | hotspot | CAGCACCCAAGGAGCTGAAG | 592504 | 52 | 78 |
| 1017650 | 1017669 | hotspot | TTTAAGAGGCTGAAGAATTA | 592507 | 42 | 79 |

TABLE 2

| Target Start Site | Target Stop Site | Region | Sequence | ISIS No | % upregulation | SEQ ID NO |
|---|---|---|---|---|---|---|
| 1017820 | 1017839 | hotspot | GGAAGTTTGTGGCATTGGTG | 592508 | 95 | 80 |
| 1018002 | 1018021 | hotspot | TGATTGAGGATTCAAAACAA | 592509 | 65 | 81 |
| 1018172 | 1018191 | hotspot | TTATTACAAGGGTCAAAAGA | 592510 | 38 | 82 |
| 1018342 | 1018361 | hotspot | GTGCTAGCCAGTGTAGAGTT | 592511 | 115 | 83 |
| 1018516 | 1018535 | hotspot | TGCCAGATGGAATTGGTCTG | 592512 | 66 | 84 |
| 1018687 | 1018706 | hotspot | CTAGTGAATGAATTGGATAA | 592513 | 42 | 85 |
| 1019053 | 1019072 | hotspot | CAAACAAAAGCTTTCCACAT | 592515 | 159 | 86 |
| 1019228 | 1019247 | hotspot | CAAAGATGAAATATATTGGT | 592516 | 44 | 87 |
| 1019398 | 1019417 | hotspot | CGAGTCCAACAATGAACCAA | 592517 | 191 | 88 |
| 1019568 | 1019587 | hotspot | CTCAATCTTCACAAAATGTT | 592518 | 105 | 89 |
| 1019738 | 1019757 | hotspot | ATTAAAATTAAACTGATCTC | 592519 | 11 | 90 |
| 1019929 | 1019948 | hotspot | GTAGACAATAGTTCGAATAA | 592520 | 52 | 91 |
| 1020102 | 1020121 | hotspot | ACCCTACCTCAACAAAGAGC | 592521 | 78 | 92 |
| 1020285 | 1020304 | hotspot | AACAAGGAATATTATGTGGG | 592522 | 61 | 93 |
| 1020480 | 1020499 | hotspot | TTTACATATACGAGCAATAA | 592523 | 15 | 94 |
| 1020650 | 1020669 | hotspot | ACGAGCCAAAATGTGACATT | 592524 | 60 | 95 |
| 1020820 | 1020839 | hotspot | TGTTGGAACTTGAATTACTA | 592525 | 123 | 96 |
| 1021024 | 1021043 | hotspot | GTGATCCTAAGTACTGAATC | 592526 | 27 | 97 |
| 1021212 | 1021231 | hotspot | GAAGCCTCTTGCAATTAATC | 592527 | 151 | 98 |
| 1021382 | 1021401 | hotspot | AAGGAACAATTTCGACTCAG | 592528 | 184 | 99 |
| 1021567 | 1021586 | hotspot | TTTTGAGAAATCACTACTAC | 592529 | 68 | 100 |
| 1021749 | 1021768 | hotspot | AATGATTGGATAGCTTGTTT | 592530 | 44 | 101 |
| 1021930 | 1021949 | hotspot | CTGGAAAAAGTGCAATTTTT | 592531 | 58 | 102 |
| 1022276 | 1022295 | hotspot | CAACAGTGAAATGACAATTT | 592532 | 28 | 103 |
| 1022446 | 1022465 | hotspot | GGAAGAATCTAGAACCTTTC | 592533 | 94 | 104 |
| 1022791 | 1022810 | hotspot | TGCTCAATTTAAATAAAAGC | 592535 | 22 | 105 |
| 1022961 | 1022980 | hotspot | GAGACAGTGATTCTCATACA | 592536 | 52 | 106 |
| 1023136 | 1023155 | hotspot | TGTGGCTTTAGAATAAGCTG | 592537 | 54 | 107 |
| 1023311 | 1023330 | hotspot | GCATGTGTAAATCAAAGCTC | 592538 | 66 | 108 |
| 1023510 | 1023529 | hotspot | ACACTGGTACTATAATTTTT | 592539 | 61 | 109 |
| 1023851 | 1023870 | hotspot | GTCTTTTAACTATTAATAAA | 592540 | 19 | 110 |
| 1024021 | 1024040 | hotspot | CCCCGAAAATTTCTGCCACT | 592541 | 135 | 111 |

TABLE 2-continued

| Target Start Site | Target Stop Site | Region | Sequence | ISIS No | % upregulation | SEQ ID NO |
|---|---|---|---|---|---|---|
| 1024192 | 1024211 | hotspot | ACTATGTGTGTGCACGCACG | 592542 | 24 | 112 |
| 1024989 | 1025008 | hotspot | GGTATGAACTCAGTTTTCTT | 592543 | 110 | 113 |
| 1025159 | 1025178 | hotspot | TGTTTCTACATAACCAACTC | 592544 | 100 | 114 |
| 1025339 | 1025358 | hotspot | AAATCCATCATGTTTTTATA | 592545 | 32 | 115 |
| 1025509 | 1025528 | hotspot | GTGTATGAAGACTCATCCTG | 592546 | 114 | 116 |
| 1025708 | 1025727 | hotspot | GGAGTGGTTTCAACTTTTCT | 592547 | 133 | 117 |
| 1025898 | 1025917 | hotspot | GTTTCCAAAACTCTTGCATC | 592548 | 120 | 118 |
| 1026088 | 1026107 | hotspot | TGAGCTACATCCCTATCCCC | 592549 | 118 | 119 |
| 1026258 | 1026277 | hotspot | ATAATTGAAATATTAACTCT | 592550 | 3 | 120 |
| 1026437 | 1026456 | hotspot | ACCATACAATGAGCAGACTG | 592551 | 108 | 121 |
| 1026607 | 1026626 | hotspot | AATTACTATCCTTTGAGAGG | 592552 | 22 | 122 |
| 1026777 | 1026796 | hotspot | TAAGTCACATTCTTTGTGTA | 592553 | 29 | 123 |
| 1026947 | 1026966 | hotspot | GATTGTTGCTATAGTTGCAG | 592554 | 62 | 124 |
| 1027117 | 1027136 | hotspot | TTGGGTTGAGATAAGTAGCT | 592555 | 84 | 125 |
| 1027287 | 1027306 | hotspot | GTTTAAAATGAACGACTTGT | 592556 | 93 | 126 |
| 1027459 | 1027478 | hotspot | TAGGAGGACCTGAGCAGGAG | 592557 | 75 | 127 |
| 1027629 | 1027648 | hotspot | CCAAGAAGGTAAATTCTGAA | 592558 | 88 | 128 |
| 1027799 | 1027818 | hotspot | GCCATACATATATCATTATT | 592559 | 118 | 129 |
| 1027971 | 1027990 | hotspot | TTGAAATAATATACTTTGAA | 592560 | 3 | 130 |
| 1028485 | 1028504 | hotspot | ATTGAAGTGGCAAGAGTGTA | 592563 | 51 | 131 |
| 1028655 | 1028674 | hotspot | TGTATTAACCTTATATACTG | 592564 | 36 | 132 |
| 1029011 | 1029030 | hotspot | CATCAAGATAATTTTACCTG | 592566 | 23 | 133 |
| 1029188 | 1029207 | hotspot | CTATCTTTGTCAAAAACACG | 592567 | 70 | 134 |
| 1029389 | 1029408 | hotspot | AACACTTTGTGTACATGTTT | 592568 | 40 | 135 |
| 1029559 | 1029578 | hotspot | TCCACAAAGCAATGAGTTCA | 592569 | 85 | 136 |
| 1029736 | 1029755 | hotspot | TCCAGAGCATTTCATCGCTG | 592570 | 133 | 137 |
| 1029908 | 1029927 | hotspot | AAGACTTATTTTCTAAAACC | 592571 | 6 | 138 |
| 1030078 | 1030097 | hotspot | TCCCTTGACTTGGATTATAC | 592572 | 93 | 139 |
| 1030248 | 1030267 | hotspot | AAATTAAGATTATTATGCTG | 592573 | 7 | 140 |
| 1030418 | 1030437 | hotspot | CCTTCATTTTCACAAAGCCA | 592574 | 150 | 141 |
| 1030607 | 1030626 | hotspot | GCAACTGATACCTTAATTCG | 592575 | 93 | 142 |
| 1030777 | 1030796 | hotspot | GAATAGAGTTTCTGGAATCA | 592576 | 102 | 143 |
| 1030986 | 1031005 | hotspot | AGGAGGCCTTCAGAAGTGCG | 592577 | 101 | 144 |
| 1031156 | 1031175 | hotspot | AAAATTCCTTTTTAGATTAA | 592578 | 17 | 145 |
| 1031326 | 1031345 | hotspot | ATTTACTCAGGTTATCTTCC | 592579 | 81 | 146 |
| 1031505 | 1031524 | hotspot | TCCACATAAACATGGAAGGA | 592580 | 26 | 147 |
| 1031845 | 1031864 | hotspot | ATCCCAACTCATAGACACCT | 592582 | 134 | 148 |
| 1032185 | 1032204 | hotspot | TAGTAACTTCCATTTGCTGC | 592583 | 118 | 149 |
| 1032355 | 1032374 | hotspot | AATCAACCTCTTTTAAAGAA | 592584 | 9 | 150 |

TABLE 2-continued

| Target Start Site | Target Stop Site | Region | Sequence | ISIS No | % upregulation | SEQ ID NO |
|---|---|---|---|---|---|---|
| 1032525 | 1032544 | hotspot | AATTCATTTGCAATAACCTT | 592585 | 41 | 151 |
| 1032695 | 1032714 | hotspot | GATTGTCATGGAACAATACT | 592586 | 64 | 152 |
| 1032873 | 1032892 | hotspot | TTCAAATGATAATATAGATT | 592587 | 10 | 153 |

TABLE 3

| Target Start Site | Target Stop Site | Region | Sequence | ISIS No | % upregulation | SEQ ID NO |
|---|---|---|---|---|---|---|
| 997638 | 997657 | hotspot | GAAATTCCCAAGAGTAGAAT | 592398 | 0 | 154 |
| 997810 | 997829 | hotspot | GGCTCAGAATTGAAACCAAA | 592399 | 142 | 155 |
| 997998 | 998017 | hotspot | ATACTAAAAATGTCATCTTC | 592400 | 19 | 156 |
| 998168 | 998187 | hotspot | CCAGCCTTGTTGGATATCAT | 592401 | 147 | 157 |
| 998338 | 998357 | hotspot | TGAGGTTCAGTAAGAGCCCC | 592402 | 178 | 158 |
| 998518 | 998537 | hotspot | GATCCATTTGTGTTAAGCTG | 592403 | 111 | 159 |
| 998688 | 998707 | hotspot | AGGTATTTCGAGTGTGATTA | 592404 | 224 | 160 |
| 998870 | 998889 | hotspot | TACCATAGAGAAACCTAATT | 592405 | 83 | 161 |
| 999040 | 999059 | hotspot | TGGGACTTAATGACCTTGGA | 592406 | 151 | 162 |
| 999213 | 999232 | hotspot | GTCCCAGAAAAGAATCTCTC | 592407 | 145 | 163 |
| 999393 | 999412 | hotspot | TCAGTCCAGCTCTTTAGTTC | 592408 | 199 | 164 |
| 999733 | 999752 | hotspot | TTGGATCCTTAAAATTTTAG | 592409 | 30 | 165 |
| 999903 | 999922 | hotspot | GAATTTATTATTGCATGGTG | 592410 | 122 | 166 |
| 1000100 | 1000119 | hotspot | GCATGAAATTGTCAAAGAAC | 592411 | 104 | 167 |
| 1000270 | 1000289 | hotspot | AATGGATAATTCTGAAGTCT | 592412 | 46 | 168 |
| 1000440 | 1000459 | hotspot | AGCTCATAGTACCAGTGGCT | 592413 | 145 | 169 |
| 1000626 | 1000645 | hotspot | CATGGTCATGAAAACAAGTA | 592414 | 100 | 170 |
| 1000796 | 1000815 | hotspot | TAGTGACATAGTTTTATGGT | 592415 | 62 | 171 |
| 1000971 | 1000990 | hotspot | GTATACCATTCATATTTCTA | 592416 | 188 | 172 |
| 1001141 | 1001160 | hotspot | AAGAAACACTGAGAGCCTGA | 592417 | 142 | 173 |
| 1001313 | 1001332 | hotspot | ATTAGGCTTATTGATGTCTG | 592418 | 127 | 174 |
| 1001483 | 1001502 | hotspot | AATACAATATTATTGCCATG | 592419 | 36 | 175 |
| 1001830 | 1001849 | hotspot | GATTAGGTGTGCTTTCAGAC | 592421 | 157 | 176 |
| 1002002 | 1002021 | hotspot | CGGGTTAGAGGAAGAATTAT | 592422 | 15 | 177 |
| 1002172 | 1002191 | hotspot | TATAAGCCACAAACATCTTG | 592423 | 148 | 178 |
| 1002355 | 1002374 | hotspot | TCATTGTGACAGTAAAGAAA | 592424 | 106 | 179 |
| 1002525 | 1002544 | hotspot | TAACTGGGTTAATTTACTAC | 592425 | 49 | 180 |
| 1002695 | 1002714 | hotspot | TATGTAGGAACATTTTTAGT | 592426 | 43 | 181 |
| 1002894 | 1002913 | hotspot | ACCAGTTGATCATGTTTTAT | 592427 | 95 | 182 |
| 1033418 | 1033437 | antisense to Ube3a pre-mRNA | TACAAGCTACAGATAACCTG | 592348 | 32 | 183 |

TABLE 3-continued

| Target Start Site | Target Stop Site | Region | Sequence | ISIS No | % upregulation | SEQ ID NO |
|---|---|---|---|---|---|---|
| 1037625 | 1037644 | antisense to Ube3a pre-mRNA | TGAGAGACATTTGTCTCTGG | 592351 | 30 | 184 |
| 1039051 | 1039070 | antisense to Ube3a pre-mRNA | ATTTCTACATGGTCATTCCT | 592352 | 59 | 185 |
| 1046085 | 1046104 | antisense to Ube3a pre-mRNA | AGATGTCTATACTAAGAAAC | 592356 | 2 | 186 |
| 1047501 | 1047520 | antisense pre-mRNA antisense | CAACTTAATTGCTTTTTGAA | 592357 | 16 | 187 |
| 1050351 | 1050370 | antisense to Ube3a pre-mRNA | GATACATTATCATTGTTATA | 592358 | 10 | 188 |
| 1051751 | 1051770 | antisense to Ube3a pre-mRNA | TCTGGTTTTCTCAAGTTCAG | 592359 | 49 | 189 |
| 1053151 | 1053170 | antisense to Ube3a pre-mRNA | ACAGTTGATATGTGTGTGGC | 592360 | 39 | 190 |
| 1054551 | 1054570 | antisense to Ube3a pre-mRNA | GCTTAATTGTCCTTGAGACC | 592361 | 41 | 191 |
| 1055951 | 1055970 | antisense to Ube3a pre-mRNA | AGTGTCAGACCTACCTATTA | 592362 | 36 | 192 |
| 1057351 | 1057370 | antisense to Ube3a pre-mRNA | GGCGGGTTGTATTTTGAGAG | 592363 | 0 | 193 |
| 1058771 | 1058790 | antisense to Ube3a pre-mRNA | GCAACAAGAACTTGATTTAA | 592364 | 35 | 194 |
| 1060171 | 1060190 | antisense to Ube3a pre-mRNA | GTAGGCGAGTAAATTAGAAT | 592365 | 20 | 195 |
| 1062997 | 1063016 | antisense to Ube3a pre-mRNA | ACTAGAAACCGAACTTGGCG | 592366 | 31 | 196 |
| 1064397 | 1064416 | antisense to Ube3a pre-mRNA | GGAATACATAAGATGAGTCA | 592367 | 28 | 197 |
| 1065809 | 1065828 | antisense to Ube3a pre-mRNA | AAAAGTTTCTTTACTTAAC | 592368 | 0 | 198 |
| 1067235 | 1067254 | antisense to Ube3a pre-mRNA | AGGACTGGTATTTAGTTTGT | 592369 | 14 | 199 |
| 1068635 | 1068654 | antisense pre-mRNA antisense | CATGAAGTTTTAGAATGAAA | 592370 | 0 | 200 |
| 1070036 | 1070055 | antisense to Ube3a pre-mRNA | GCATATCCATTTTCAATAAA | 592371 | 11 | 201 |
| 1071436 | 1071455 | antisense to Ube3a pre-mRNA | AAAAGGCATATTTTTATTT | 592372 | 0 | 202 |

TABLE 3-continued

| Target Start Site | Target Stop Site | Region | Sequence | ISIS No | % upregulation | SEQ ID NO |
|---|---|---|---|---|---|---|
| 1072836 | 1072855 | antisense to Ube3a pre-mRNA | TACTTTCAGTCTTGTAATAC | 592373 | 20 | 203 |
| 1074250 | 1074269 | antisense to Ube3a pre-mRNA | GATTTCCAATATTCTTCATC | 592374 | 10 | 204 |
| 1075650 | 1075669 | antisense to Ube3a pre-mRNA | CCAAACAATTTTCAGATATA | 592375 | 1 | 205 |
| 1077065 | 1077084 | antisense to Ube3a pre-mRNA | GGTATTTTCCTCAATTACAT | 592376 | 23 | 206 |
| 1078467 | 1078486 | antisense to Ube3a pre-mRNA | GCCACCATATGGTTGCTGGG | 592377 | 147 | 207 |
| 1079867 | 1079886 | antisense to Ube3a pre-mRNA | CAGGCATAAGAGTCAGAAGC | 592378 | 24 | 208 |
| 1081267 | 1081286 | antisense to Ube3a pre-mRNA | TTGAGGAAGAGGGCTAATTT | 592379 | 2 | 209 |
| 1084067 | 1084086 | antisense to Ube3a pre-mRNA | GTTTTCCAGTGAGTACCAGC | 592380 | 4 | 210 |
| 1085491 | 1085510 | antisense to Ube3a pre-mRNA | TAACTAGAGGAATACCAACT | 592381 | 2 | 211 |
| 1086900 | 1086919 | antisense to Ube3a pre-mRNA | GAAAGCATCCTTAGTTTCTC | 592382 | 9 | 212 |
| 1088316 | 1088335 | antisense to Ube3a pre-mRNA | TTGCAGCATTAATTAAACAA | 592383 | 9 | 213 |
| 1091119 | 1091138 | antisense to Ube3a pre-mRNA | GGCAATTAAATTCTACTTTT | 592384 | 1 | 214 |
| 1093920 | 1093939 | antisense to Ube3a pre-mRNA | CTGGAGTTTGTGATGGTTGT | 592386 | 9 | 215 |
| 1095320 | 1095339 | antisense to Ube3a pre-mRNA | AGGATATATTTTGGCAACTT | 592387 | 0 | 216 |
| 1096720 | 1096739 | antisense to Ube3a pre-mRNA | TTTATCAGAAATGCCTGGGA | 592388 | 1 | 217 |
| 1099541 | 1099560 | antisense to Ube3a pre-mRNA | GTCCATCTATCAATTTATTA | 592389 | 22 | 218 |
| 1100945 | 1100964 | antisense to Ube3a pre-mRNA | TTTAAATAGCTGATTATCTG | 592390 | 4 | 219 |
| 1102346 | 1102365 | antisense to Ube3a pre-mRNA | CAAGAGATAATAGCTTAATT | 592391 | 6 | 220 |
| 1103750 | 1103769 | antisense to Ube3a pre-mRNA | ATTAGTTGATACCACTCTTC | 592392 | 23 | 221 |

TABLE 3-continued

| Target Start Site | Target Stop Site | Region | Sequence | ISIS No | % upregulation | SEQ ID NO |
|---|---|---|---|---|---|---|
| 1105150 | 1105169 | antisense to Ube3a pre-mRNA | AGTGAAACCAGAGTAGTAGT | 592393 | 3 | 222 |
| 1106554 | 1106573 | antisense to Ube3a pre-mRNA | CATGTGGTATATATAAAATG | 592394 | 0 | 223 |
| 1107954 | 1107973 | antisense to Ube3a pre-mRNA | AGCCTAGACTAAGAGGCGAG | 592395 | 0 | 224 |
| 1109354 | 1109373 | antisense to Ube3a pre-mRNA | GCTAAATATCAAAGCCCTAT | 592396 | 8 | 225 |

Example 2

Antisense Inhibition of the Antisense Sequence of Ubiquitin Protein Ligase E3A (Ube3a-ATS) in Primary Neuronal Cells Antisense oligonucleotides selected from the study described above were tested for their effects on inhibiting the expression of Ube3a-ATS mRNA in vitro.

Primary neuronal cultures from Ube3a-YFP paternal$^{+/-}$ mice were prepared, as described above. Cells were seeded on poly-D-lysine-coated 24-well plates at a density of 2.5× $10^5$ cells/cm$^2$ in 500 µL of culture medium. At day 4, 400 µL medium was removed from sets of wells and 100 µL of fresh medium, along with 10 µM antisense oligonucleotide and 2 µM Ara-C were added. A set of cells treated with PBS was used as the untreated control. At day 7, the sets were washed with PBS twice and RNA isolation was conducted.

Total RNA was prepared with miRNAeasy Mini Kit (Qiagen, Valencia, Calif.). On-column DNase treatment was performed for all the samples. mRNA was purified from total RNA with oligo(dT) beads supplied in Illumina mRNA-seq Sample Preparation Kit, according to the manufacturer's instructions (Illumina, San Diego, Calif.). cDNA was then generated with SuperScript III First-Strand Synthesis System (Invitrogen) and q-PCR was performed using Applied Biosystems StepOnePlus Real-Time PCR System and SYBR Green Master Mix (Applied Biosystems, Carlsbad, Calif.).

The results are presented in Table 4, expressed as a percentage of the untreated control. The data indicates that treatment with antisense oligonucleotides targeted to the hotspot region that we identified results in marked inhibition of the Ube3a-YFP-ATS mRNA transcript and correspondingly induces expression of the paternal Ube3a-YFP transcript.

TABLE 4

% expression of mRNA transcript expression relative to the untreated control

|  | % inhibition of Ube3a-YFP-ATS | % induction of Ube3a-YFP |
|---|---|---|
| ISIS 592467 | 88 ± 2 | 71 ± 23 |
| ISIS 592517 | 94 ± 5 | 128 ± 5 |
| ISIS 592528 | 81 ± 9 | 288 ± 71 |
| ISIS 592404 | 94 ± 4 | 137 ± 12 |

Example 3

Dose-Dependent Antisense Inhibition of Ube3a-ATS and Up-Regulation of Paternal Ube3a in Primary Neuronal Cells Antisense oligonucleotides selected from the study described above were tested for their effects on inhibiting the expression of Ube3a-ATS mRNA and up-regulating the expression of paternal Ube3a in vitro. The effect on snoRNA genes near the hotspot region and some of which have been shown to be involved in Prader-Willi syndrome (Sahoo, T. et al., Nat. Genet. 2008. 40: 719-21; Tsai, T. et al., Hum. Mol. Genet. 1999. 8: 1357-64) was also assessed.

Primary neuronal cultures from Ube3a-YFP paternal$^{+/-}$ mice were prepared, as described above, and transfected with 39 nM, 156 nM, 625 nM, 2,500 nM, or 10,000 nM concentrations of antisense oligonucleotide. The cells were separately treated with the topoisomerase inhibitor, Topotecan, at 1.17 nM, 4.69 nM, 18.75 nM, 75.00 nM, or 300.00 nM concentrations. Total RNA was prepared with RNeasy 96 Kit (Qiagen). On-column DNase treatment was performed for all the samples. qRT-PCR was performed using EXPRESS One-Step SuperScript qRT-PCR Kit (Qiagen) and EXPRESS One-Step SYBR GreenER Kit (Qiagen).

The results are presented in Tables 5 and 6, expressed as a percentage of the untreated control. The data indicates that treatment with antisense oligonucleotides targeted to the hotspot region that we identified resulted in marked inhibition of the Ube3a-YFP-ATS transcript and correspondingly induced expression of the paternal Ube3a-YFP transcript. Treatment with Topotecan also inhibited Ube3a-YFP-ATS transcript levels and induced the expression of Ube3a-YFP mRNA as expected. Several of ISIS antisense oligonucleotides inhibited Ube3a-YFP-ATS and up-regulated Ube3a-YFP mRNA levels.

The cells were also assessed for the induction of Ube3a-YFP protein, as quantified by fluorescence, using the method described in Example 1. The results are presented in Table 7, and demonstrate that treatment with antisense oligonucleotides targeted to the hotspot region that we identified resulted in an increase in Ube3a-YFP protein levels, as indicated by increased YFP fluorescence. Treatment with Topotecan also induced the expression of Ube3a-YFP protein levels, as expected. The expression levels of the MBII-85 and MBII-52 snoRNAs and Snrpn were also evaluated. The results are presented in Tables 8-10. The data indicates that treatment with antisense oligonucleotides targeted to the hotspot region resulted in minimal reduction in these snoRNA genes, the reduction of which is associated with Prader-Willi syndrome. By contrast, treatment with Topotecan reduced the levels of the snoRNA gene MBII-52, and Snrpn levels.

TABLE 5

% inhibition of Ube3a-YFP-ATS transcript expression relative to the untreated control

| ISIS No | 39 nM | 156 nM | 625 nM | 2,500 nM | 10,000 nM |
|---|---|---|---|---|---|
| 592401 | 0 | 0 | 40 | 68 | 91 |
| 592404 | 32 | 50 | 78 | 93 | 96 |
| 592408 | 29 | 40 | 49 | 67 | 75 |
| 592413 | 34 | 43 | 63 | 75 | 85 |
| 592482 | 0 | 16 | 55 | 86 | 94 |
| 592483 | 19 | 49 | 62 | 91 | 96 |
| 592489 | 0 | 33 | 62 | 85 | 93 |
| 592515 | 6 | 37 | 69 | 87 | 91 |
| 592517 | 12 | 66 | 71 | 89 | 96 |
| 592528 | 0 | 59 | 77 | 92 | 93 |
| Small molecule inhibitor | 1.17 nM | 4.69 nM | 18.75 nM | 75.00 nM | 300.00 nM |
| Topotecan | 23 | 33 | 50 | 73 | 88 |

TABLE 6

% Ube3a-YFP transcript expression relative to the untreated control

| ISIS No | 39 nM | 156 nM | 625 nM | 2,500 nM | 10,000 nM |
|---|---|---|---|---|---|
| 592401 | 103 | 183 | 305 | 753 | 955 |
| 592404 | 151 | 260 | 499 | 890 | 810 |
| 592408 | 89 | 97 | 189 | 240 | 616 |
| 592413 | 136 | 145 | 254 | 556 | 764 |
| 592482 | 142 | 167 | 372 | 697 | 1277 |
| 592483 | 150 | 163 | 237 | 607 | 852 |
| 592489 | 149 | 188 | 215 | 514 | 646 |
| 592515 | 145 | 136 | 192 | 467 | 705 |
| 592517 | 151 | 189 | 237 | 528 | 821 |
| 592528 | 215 | 268 | 378 | 715 | 639 |
| Small molecule inhibitor | 1.17 nM | 4.69 nM | 18.75 nM | 75.00 nM | 300.00 nM |
| Topotecan | 124 | 127 | 193 | 430 | 734 |

TABLE 7

% Ube3a-YFP protein expression relative to the untreated control

| ISIS No | 39 nM | 156 nM | 625 nM | 2,500 nM | 10,000 nM |
|---|---|---|---|---|---|
| 592401 | 95 | 102 | 109 | 154 | 193 |
| 592404 | 95 | 108 | 153 | 183 | 262 |
| 592408 | 100 | 96 | 105 | 134 | 173 |
| 592413 | 107 | 104 | 109 | 126 | 185 |
| 592482 | 95 | 110 | 130 | 135 | 201 |
| 592483 | 94 | 109 | 97 | 148 | 202 |
| 592489 | 102 | 105 | 104 | 132 | 177 |
| 592515 | 101 | 112 | 104 | 134 | 177 |
| 592517 | 97 | 104 | 121 | 137 | 211 |
| 592528 | 102 | 121 | 117 | 146 | 207 |
| Small molecule inhibitor | 1.17 nM | 4.69 nM | 18.75 nM | 75.00 nM | 300.00 nM |
| Topotecan | 102 | 112 | 139 | 217 | 290 |

TABLE 8

% MBII-85 transcript expression relative to the untreated control

| ISIS No | 39 nM | 156 nM | 625 nM | 2,500 nM | 10,000 nM |
|---|---|---|---|---|---|
| 592401 | 96 | 114 | 118 | 122 | 125 |
| 592404 | 108 | 79 | 87 | 101 | 93 |
| 592408 | 83 | 66 | 81 | 75 | 81 |
| 592413 | 74 | 72 | 68 | 79 | 85 |
| 592482 | 121 | 91 | 81 | 106 | 88 |
| 592483 | 84 | 84 | 91 | 97 | 102 |
| 592489 | 74 | 78 | 100 | 94 | 69 |
| 592515 | 66 | 108 | 93 | 88 | 118 |
| 592517 | 54 | 73 | 94 | 74 | 98 |
| 592528 | 81 | 98 | 119 | 139 | 115 |
| Small molecule inhibitor | 1.17 nM | 4.69 nM | 18.75 nM | 75.00 nM | 300.00 nM |
| Topotecan | 93 | 84 | 79 | 67 | 85 |

TABLE 9

% MBII-52 transcript expression relative to the untreated control

| ISIS No | 39 nM | 156 nM | 625 nM | 2,500 nM | 10,000 nM |
|---|---|---|---|---|---|
| 592401 | 98 | 138 | 106 | 112 | 86 |
| 592404 | 91 | 66 | 73 | 63 | 31 |
| 592408 | 94 | 62 | 97 | 89 | 75 |
| 592413 | 80 | 83 | 92 | 104 | 82 |
| 592482 | 107 | 94 | 87 | 95 | 63 |
| 592483 | 104 | 102 | 103 | 100 | 97 |
| 592489 | 106 | 98 | 101 | 99 | 87 |
| 592515 | 100 | 103 | 104 | 104 | 120 |
| 592517 | 109 | 95 | 106 | 95 | 92 |
| 592528 | 106 | 119 | 143 | 131 | 111 |
| Small molecule inhibitor | 1.17 nM | 4.69 nM | 18.75 nM | 75.00 nM | 300.00 nM |
| Topotecan | 112 | 92 | 81 | 50 | 40 |

TABLE 10

% Snrpn transcript expression relative to the untreated control

| ISIS No | 39 nM | 156 nM | 625 nM | 2,500 nM | 10,000 nM |
|---|---|---|---|---|---|
| 592401 | 93 | 127 | 107 | 133 | 114 |
| 592404 | 76 | 88 | 99 | 102 | 92 |
| 592408 | 75 | 81 | 94 | 80 | 85 |
| 592413 | 83 | 74 | 78 | 88 | 78 |
| 592482 | 126 | 105 | 105 | 74 | 46 |
| 592483 | 115 | 115 | 99 | 108 | 103 |
| 592489 | 125 | 12 | 98 | 87 | 72 |
| 592515 | 101 | 114 | 101 | 95 | 103 |

TABLE 10-continued

% Snrpn transcript expression relative to the untreated control

| ISIS No | 39 nM | 156 nM | 625 nM | 2,500 nM | 10,000 nM |
|---|---|---|---|---|---|
| 592517 | 99 | 109 | 99 | 71 | 45 |
| 592528 | 122 | 108 | 109 | 114 | 111 |
| Small molecule inhibitor | 1.17 nM | 4.69 nM | 18.75 nM | 75.00 nM | 300.00 nM |
| Topotecan | 102 | 99 | 87 | 71 | 54 |

Example 4

Comparison of the Effect of ASOs Targeting the Hotspot Region and ASOs Targeting within the Region Antisense to the Ube3a Pre-mRNA on the Up-Regulation of Paternal Ube3a Transcript in Primary Neuronal Cells To evaluate the optimal region for targeting with antisense oligonucleotides resulting in up-regulation of paternal Ube3a gene transcript, treatment with ASOs targeting the hotspot region and treatment with ASOs targeting within the region antisense to the Ube3a pre-mRNA was assessed.

Primary neuronal cultures from Ube3a-YFP paternal$^{+/-}$ mice were prepared, as described above, and transfected with 15 μM concentration of antisense oligonucleotide. Total RNA was prepared with RNeasy 96 Kit (Qiagen). On-column DNase treatment was performed for all the samples. qRT-PCR was performed using EXPRESS One-Step SuperScript qRT-PCR Kit (Qiagen) and EXPRESS One-Step SYBR GreenER Kit (Qiagen). The results are presented in Table 10, expressed as a percentage of the untreated control.

The data indicates that treatment with antisense oligonucleotides targeting both regions resulted in marked inhibition of the Ube3a-YFP-ATS mRNA transcript. However, treatment with ASOs targeting the hotspot region resulted in markedly higher upregulation of paternal Ube3a-YFP transcript expression compared to treatment with ASOs targeting the region antisense to the Ube3a pre-mRNA.

TABLE 11

% expression levels compared to the untreated control

| Target Start Site | Target Stop Site | Region | ISIS No | % expression of Ube3a-YFP-ATS | % expression of Ube3Pa-YFP | SEQ ID NO |
|---|---|---|---|---|---|---|
| 997810 | 997829 | hotspot | 592399 | 4 | 624 | 155 |
| 997998 | 998017 | hotspot | 592400 | 7 | 259 | 156 |
| 998168 | 998187 | hotspot | 592401 | 3 | 936 | 157 |
| 998688 | 998707 | hotspot | 592404 | 7 | 1139 | 160 |
| 998870 | 998889 | hotspot | 592405 | 9 | 518 | 161 |
| 999040 | 999059 | hotspot | 592406 | 7 | 644 | 162 |
| 999213 | 999232 | hotspot | 592407 | 10 | 555 | 163 |
| 999393 | 999412 | hotspot | 592408 | 6 | 670 | 164 |
| 1000270 | 1000289 | hotspot | 592412 | 14 | 827 | 168 |
| 1000440 | 1000459 | hotspot | 592413 | 16 | 576 | 169 |
| 1000971 | 1000990 | hotspot | 592416 | 10 | 802 | 172 |
| 1001141 | 1001160 | hotspot | 592417 | 15 | 935 | 173 |
| 1001830 | 1001849 | hotspot | 592421 | 12 | 1042 | 176 |
| 1002172 | 1002191 | hotspot | 592423 | 13 | 624 | 178 |
| 1002355 | 1002374 | hotspot | 592424 | 20 | 871 | 179 |
| 1033418 | 1033437 | hotspot | 592348 | 9 | 704 | 183 |
| 1046085 | 1046104 | antisense to Ube3a pre-mRNA | 592356 | 15 | 288 | 186 |
| 1057351 | 1057370 | antisense to Ube3a pre-mRNA | 592363 | 9 | 158 | 193 |
| 1058771 | 1058790 | antisense to Ube3a pre-mRNA | 592364 | 16 | 315 | 194 |
| 1062997 | 1063016 | antisense to Ube3a pre-mRNA | 592366 | 18 | 163 | 196 |
| 1072836 | 1072855 | antisense to Ube3a pre-mRNA | 592373 | 20 | 131 | 203 |
| 1078467 | 1078486 | antisense to Ube3a pre-mRNA | 592377 | 7 | 435 | 207 |
| 1085491 | 1085510 | antisense to Ube3a pre-mRNA | 592381 | 16 | 158 | 211 |
| 1086900 | 1086919 | antisense to Ube3a pre-mRNA | 592382 | 16 | 94 | 212 |
| 1099541 | 1099560 | antisense to Ube3a pre-mRNA | 592389 | 12 | 296 | 218 |
| 1100945 | 1100964 | antisense to Ube3a pre-mRNA | 592390 | 13 | 111 | 219 |
| 1102346 | 1102365 | antisense to Ube3a pre-mRNA | 592391 | 15 | 88 | 220 |
| 1103750 | 1103769 | antisense to Ube3a pre-mRNA | 592392 | 4 | 100 | 221 |
| 1109354 | 1109373 | antisense to Ube3a pre-mRNA | 592396 | 18 | 182 | 225 |

Example 5

Antisense Inhibition of the Antisense Sequence of Ube3a-ATS In Vivo

Antisense oligonucleotides, selected from the in vitro screening study described above, were screened for in vivo efficacy in wild-type C57BL6 mice.

Antisense oligonucleotide administration was accomplished by intracerebroventricular bolus injection of 300 μg in the mice. The mice were euthanized 4 weeks after the administration and the level of Ube3a-ATS mRNA down-regulation was assessed using sections from the cortex, hippocampus, and spinal cord. RNA isolation and qRT-PCR was performed as described in Example 4. The expression of MBII-85, MBII-52, and Snrpn were also evaluated.

The data is presented in Tables 12-15, normalized to the house-keeping gene, GAPDH. The results indicate that treatment with antisense oligonucleotides targeted to the hotspot region that we identified resulted in inhibition of the Ube3a-ATS mRNA transcript. Moreover, MBII-85, MBII-52, and Snrpn expression was maintained following knockdown of Ube3a-ATS.

TABLE 12

% expression of Ube3a-ATS transcript
expression relative to the untreated control

| ISIS No | Cortex | Hippocampus | Spinal Cord |
|---|---|---|---|
| 592401 | 35 | 44 | 48 |
| 592408 | 50 | 43 | 45 |
| 592413 | 38 | 45 | 67 |
| 592482 | 30 | 31 | 32 |
| 592489 | 28 | 36 | 52 |
| 592515 | 67 | 66 | 79 |
| 592517 | 39 | 43 | 44 |

TABLE 13

% expression of MBII-85 transcript
expression relative to the untreated control

| ISIS No | Cortex | Hippocampus | Spinal Cord |
|---|---|---|---|
| 592401 | 82 | 104 | 98 |
| 592408 | 99 | 96 | 112 |
| 592413 | 121 | 99 | 90 |
| 592482 | 85 | 74 | 99 |
| 592489 | 98 | 105 | 99 |
| 592515 | 101 | 100 | 92 |
| 592517 | 78 | 82 | 94 |

TABLE 14

% expression of MBII-52 transcript
expression relative to the untreated control

| ISIS No | Cortex | Hippocampus | Spinal Cord |
|---|---|---|---|
| 592401 | 90 | 103 | 92 |
| 592408 | 95 | 85 | 115 |
| 592413 | 103 | 103 | 91 |
| 592482 | 81 | 91 | 103 |
| 592489 | 135 | 118 | 124 |
| 592515 | 112 | 140 | 97 |
| 592517 | 92 | 103 | 98 |

TABLE 15

% expression of Snrpn transcript
expression relative to the untreated control

| ISIS No | Cortex | Hippocampus | Spinal Cord |
|---|---|---|---|
| 592401 | 92 | 90 | 92 |
| 592408 | 96 | 90 | 84 |
| 592413 | 97 | 97 | 80 |
| 592482 | 85 | 74 | 46 |
| 592489 | 96 | 88 | 74 |
| 592515 | 95 | 93 | 82 |
| 592517 | 88 | 87 | 49 |

Example 6

Antisense Inhibition of Ube3a-ATS in Ube3a-YFP Mice

Antisense oligonucleotides selected from the studies described above were screened for in vivo efficacy and tolerability in the Ube3a-YFP mouse model (Dindot, S. V. et al., Hum. Mol. Genet. 2008. 17: 111-118).

Antisense oligonucleotide was administered to the mice by intracerebroventricular bolus injection of 300 µg of ISIS 592401 or ISIS 592489. The mice were euthanized after 4 weeks of administration. Levels of Ube3a-YFP-ATS mRNA and Ube3a-YFP mRNA were assessed in the cortex, hippocampus and spinal cord. The assays were performed as described previously (Meng, L. et al., Hum. Mol. Genet. 2012. doi:10.1093/hmg/dds1).

RNA was isolated from the different brain sections and analyzed by qRT-PCR. The results are presented in Tables 16 and 17, normalized to GAPDH. The data indicates that ASO administration resulted in approximately 50-65% knockdown of Ube3a-YFP-ATS transcript in the brain and spinal cord. Correspondingly, there was an approximate 1.5-2-fold increase of Ube3a-YFP mRNA in ASO-treated mice. As shown in FIG. 1, Western Blot analysis was performed using an anti-YFP antibody and confirmed that treatment with ASO increased paternal Ube3a protein expression.

The expression of MBII-85, MBII-52, and Snrpn were also evaluated. As presented in Tables 18-20, MBII-85, MBII-52, and Snrpn expression was maintained following knockdown of Ube3a-YFP-ATS. Levels of the microglial marker AIF1 were also assessed as a measure of CNS toxicity. As presented in Table 21, there was negligible increase in Aif1 levels, indicating that ASO treatment was neurotolerable.

TABLE 16

% inhibition of Ube3a-YFP-ATS mRNA transcript
expression relative to untreated control

| | Cortex | Hippocampus | Spinal cord |
|---|---|---|---|
| ISIS 592401 | 48 ± 9 | 59 ± 9 | 63 ± 12 |
| ISIS 592489 | 59 ± 16 | 65 ± 5 | 64 ± 7 |

TABLE 17

% Ube3a-YFP mRNA transcript expression
relative to untreated control (denoted as 100%)

| | Cortex | Hippocampus | Spinal cord |
|---|---|---|---|
| ISIS 592401 | 169 ± 7 | 198 ± 22 | 176 ± 72 |
| ISIS 592489 | 140 ± 31 | 156 ± 22 | 142 ± 22 |

TABLE 18

% MBII-85 mRNA transcript expression
relative to untreated control (denoted as 100%)

| | Cortex | Hippocampus | Spinal cord |
|---|---|---|---|
| ISIS 592401 | 107 ± 13 | 114 ± 3 | 108 ± 11 |
| ISIS 592489 | 73 ± 25 | 102 ± 5 | 109 ± 16 |

TABLE 19

% MBII-52 mRNA transcript expression
relative to untreated control (denoted as 100%)

| | Cortex | Hippocampus | Spinal cord |
|---|---|---|---|
| ISIS 592401 | 75 ± 1 | 99 ± 0 | 83 ± 13 |
| ISIS 592489 | 95 ± 33 | 109 ± 9 | 91 ± 13 |

TABLE 20

% Snrpn mRNA transcript expression
relative to untreated control (denoted as 100%)

| | Cortex | Hippocampus | Spinal cord |
|---|---|---|---|
| ISIS 592401 | 103 ± 3 | 95 ± 4 | 91 ± 7 |
| ISIS 592489 | 94 ± 12 | 90 ± 6 | 92 ± 5 |

TABLE 21

% Aif1 mRNA transcript expression
relative to untreated control (denoted as 100%)

| | Cortex | Hippocampus | Spinal cord |
|---|---|---|---|
| ISIS 592401 | 94 ± 4 | 106 ± 7 | 111 ± 5 |
| ISIS 592489 | 92 ± 11 | 112 ± 21 | 182 ± 30 |

Example 7

Antisense Inhibition of Ube3a-ATS in Ube3a-YFP Mice

Antisense oligonucleotides selected from the studies described above were screened for in vivo efficacy and tolerability in the Ube3a-YFP mouse model (Dindot, S. V. et al., Hum. Mol. Genet. 2008. 17: 111-118).

Antisense oligonucleotide was administered to the mice by intracerebroventricular bolus injection of 500 µg of ISIS 592401. The mice were euthanized after 4 weeks of administration. Levels of Ube3a-YFP-ATS mRNA, Ube3a-YFP mRNA and Ube3a protein were assessed in the cortex, hippocampus and spinal cord. The assays were performed as described previously (Meng, L. et al., Hum. Mol. Genet. 2012. doi:10.1093/hmg/dds1).

Figure 2:
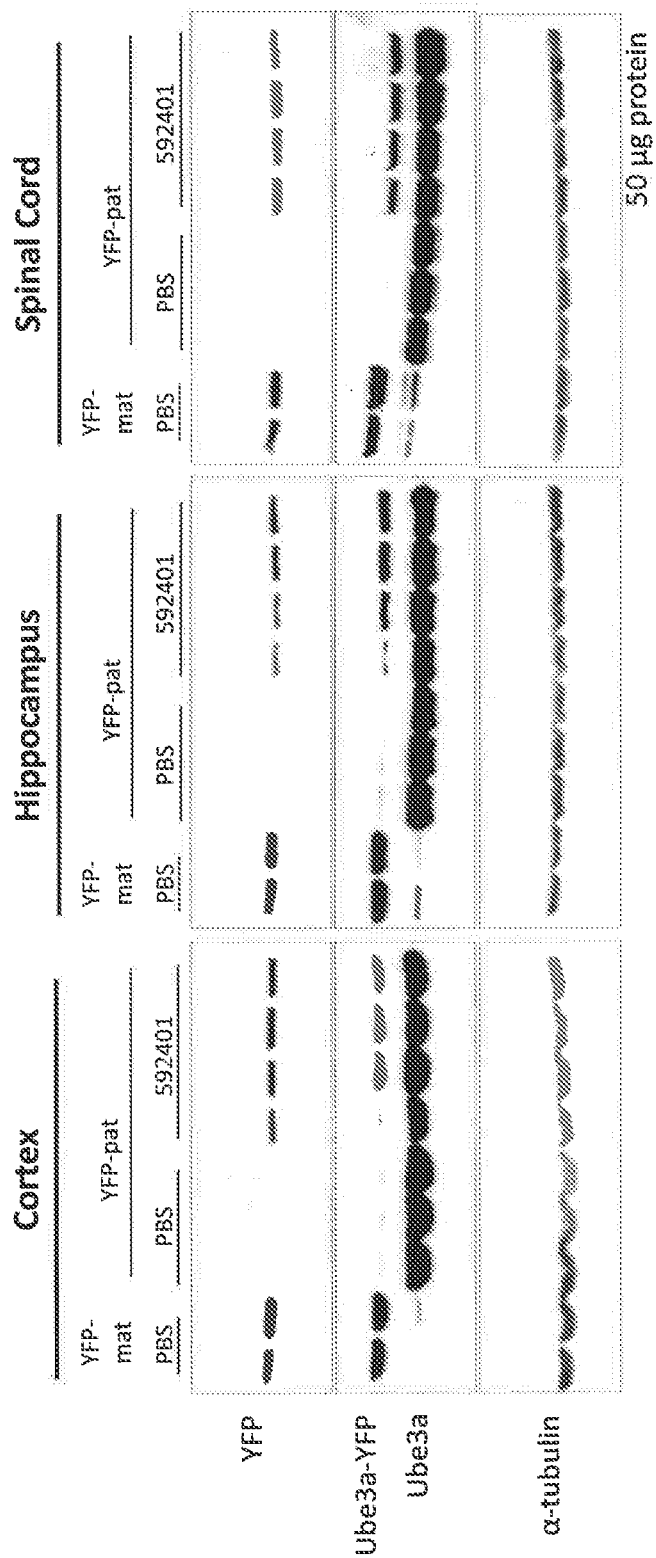
FIG. 2 shows Western Blot analysis using an anti-YFP antibody, which confirmed that treatment with ASO increased paternal Ube3a protein expression.

RNA was isolated from the different brain sections and analyzed by qRT-PCR. The results are presented in Tables 22 and 23, normalized to GAPDH. The data indicates that ASO administration resulted in approximately 65-85% knockdown of Ube3a-YFP-ATS transcript in the brain and spinal cord. Correspondingly, there was an approximate 2.5 to 4.5-fold increase of Ube3a-YFP mRNA in ASO-treated mice. As shown in FIG. 2, Western Blot analysis was performed using an anti-YFP antibody and confirmed that treatment with ASO increased paternal Ube3a protein expression.

The expression of MBII-85, MBII-52, and Snrpn were also evaluated. As presented in Tables 24-26, MBII-85, MBII-52, and Snrpn expression was minimally affected following knockdown of Ube3a-YFP-ATS. Levels of the microglial marker AIF1 were also assessed as a measure of CNS toxicity. As presented in Table 27, there was negligible increase in Aif1 levels, indicating that ASO treatment was neurotolerable.

TABLE 22

% inhibition of Ube3a-YFP-ATS mRNA transcript
expression relative to untreated control

| | Cortex | Hippocampus | Spinal cord |
|---|---|---|---|
| ISIS 592401 | 84 ± 6 | 66 ± 4 | 69 ± 1 |

TABLE 23

% Ube3a-YFP mRNA transcript expression
relative to untreated control (denoted as 100%)

| | Cortex | Hippocampus | Spinal cord |
|---|---|---|---|
| ISIS 592401 | 445 ± 81 | 263 ± 8 | 284 ± 25 |

TABLE 24

% MBII-85 mRNA transcript expression
relative to untreated control (denoted as 100%)

| | Cortex | Hippocampus | Spinal cord |
|---|---|---|---|
| ISIS 592401 | 65 ± 183 | 98 ± 12 | 98 ± 7 |

TABLE 25

% MBII-52 mRNA transcript expression
relative to untreated control (denoted as 100%)

| | Cortex | Hippocampus | Spinal cord |
|---|---|---|---|
| ISIS 592401 | 72 ± 17 | 92 ± 8 | 89 ± 10 |

TABLE 26

% Snrpn mRNA transcript expression
relative to untreated control (denoted as 100%)

| | Cortex | Hippocampus | Spinal cord |
|---|---|---|---|
| ISIS 592401 | 102 ± 11 | 101 ± 3 | 95 ± 2 |

TABLE 27

% Aif1 mRNA transcript expression
relative to untreated control (denoted as 100%)

| | Cortex | Hippocampus | Spinal cord |
|---|---|---|---|
| ISIS 592401 | 104 ± 13 | 80 ± 8 | 113 ± 14 |

Example 8

Antisense Inhibition of Ube3a-ATS in Mice Having Maternal Deficiency in Ube3a Antisense oligonucleotides selected from the studies described above will be screened for in vivo efficacy in a genetic mouse model of Angelman Syndrome described in Jiang, Y. et al., Neuron. 1998. 21: 799-811. The mice have a null mutation in the maternal Ube3a allele. A targeting vector replaces a 3 kb genomic DNA fragment containing exon 2 (299 bp; 3-302 bp in GENBANK Accession No. U82122) of the maternal Ube3a allele, thereby deleting one hundred of the most N terminal amino acids, shifting the reading frame, and inactivating all putative isoforms of maternal Ube3a. The mice have normal neuroanatomy but display a deficiency in context-dependent learning long-term potentiation (LTP), motor dysfunction, and inducible seizures similar to human Angelman Syndrome.

Antisense oligonucleotides described herein are administered to the mice by intracerebroventricular bolus injection at a dose range from 10 µg to 1 mg final concentration. The mice are euthanized and the levels of Ube3a-ATS mRNA down-regulation as well as Ube3a protein induction are assessed using hippocampus or whole brain sections.

Mice treated with ASOs are assessed by various phenotypic and behavioral assays for treatment or amelioration of the phenotypic defects. The open field assay as described in Miller, B. H. et al., PloS One. 2010. 5: e14458 is conducted to assess whether the hypoactive phenotype is treated by ASO administration. The marble burying assay as described in Njung'e, K. and Handley, S. L. Pharmacol. Biochem. Behav. 1991. 38: 63-67 is conducted to assess whether anxiety in the mice is treated by ASO administration. The rotarod assay and the dowel test as described in Chen, M. and Xu, R. BMC Neurosci. 2011. 12: 1 is conducted to assess for improvements in the balance and motor functions of the mice by ASO administration.

Mice treated with ASOs are tested for motor function using footprint analysis. The hindpaws of the mice are dipped into red waterproof ink and the mice are placed at an open end of a dark tunnel. The step length, step width, and left-right alternation coefficient are calculated as described in Clark, H. B. et al., J. Neurosci. 1997. 17: 7385-7395.

Mice treated with ASOs are tested for reduction in seizures by an assay involving scratching a plastic pen across a stainless steel cage, grating as rapidly and intensively as possible, until seizures occur or for a maximum of 45 sec. Each animal will be tested once between 5 and 10 weeks of age. EEG recordings will be performed, as described in Cattanach, B. M. et al., Mamm. Genome 1997. 8: 472-478.

Mice treated with ASOs are tested for improvement in context dependent learning with the fear conditioning assay, which uses a standard testing chamber with a stainless steel grated floor through which scrambled foot shock is administered. Freezing will be assessed and scored as either 1 (freezing posture) or 0 (non-freezing posture). The scores will be averaged over a 1 minute interval and converted into percentages.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09617539B2). An electronic copy of the "Sequence Listing" will also be available from the USPTO upon request and payment of the fee set forth in 37 CFR 1.19(b)(3).

What is claimed:

1. A method of treating Angelman syndrome in an animal comprising administering to an animal with Angelman syndrome an antisense compound targeted to UBE3A-ATS, wherein the antisense compound comprises an oligonucleotide consisting of 12 to 30 linked nucleosides, wherein the oligonucleotide is at least 85% complementary to a sequence within nucleobases 446213 to 513602 of SEQ ID NO: 2.

2. The method of claim 1, wherein UBE3A-ATS comprises a nucleic acid sequence at least 85% identical to SEQ ID NO:2.

3. The method of claim 1, wherein the oligonucleotide is at least 90% complementary over its entire length to an equal length region of a UBE3A-ATS nucleic acid sequence.

4. The method of claim 1, wherein the oligonucleotide is at least 95% complementary over its entire length to an equal length region of a UBE3A-ATS nucleic acid sequence.

5. The method of claim 1, wherein the oligonucleotide is 100% complementary over its entire length to an equal length region of a UBE3A-ATS nucleic acid sequence.

6. The method of claim 1, wherein the oligonucleotide is a single-stranded oligonucleotide.

7. The method of claim 6, wherein the oligonucleotide is a modified oligonucleotide.

8. The method of claim 7, wherein the modified oligonucleotide comprises at least one modified internucleoside linkage.

9. The method of claim 8, wherein the modified internucleoside linkage is a phosphorothioate internucleoside linkage.

10. The method of claim 7, wherein at least one nucleoside comprises a modified sugar.

11. The method of claim 10, wherein the modified sugar is a bicyclic sugar comprising a bridge between the 4' and the 2' positions of the sugar.

12. The method of claim 11, wherein the bridge is selected from 4'-CH(CH$_3$)—O-2', 4'-CH$_2$-2', 4'-(CH$_2$)$_2$-2', 4'-CH$_2$—O-2', 4'-(CH$_2$)$_2$—O-2', 4'-CH$_2$—O—N(R$_1$)-2' and 4'-CH2-N(R$_1$)—O-2'- wherein each R1 is, independently, H, a protecting group or C1-C12 alkyl.

13. The method of claim 12, wherein the bridge is 4'-CH(CH$_3$)—O-2'.

14. The method of claim 12, wherein the bridge is selected from 4'-CH$_2$—O-2' and 4'-(CH$_2$)$_2$—O-2'.

15. The method of claim 10, wherein the modified sugar comprises a 2'-O-methoxyethyl group.

16. The method of claim 7, wherein at least one nucleoside comprises a modified nucleobase.

* * * * *